United States Patent
Matlock

(10) Patent No.: US 7,476,242 B2
(45) Date of Patent: Jan. 13, 2009

(54) ELECTRICALLY HEATED/PHASE CHANGE PROBE TEMPERATURE CONTROL

(75) Inventor: George Matlock, Pleasanton, CA (US)

(73) Assignee: AMS Research Corporation, Minnetonka, MN (US)

( * ) Notice: Subject to any disclaimer, the term of this patent is extended or adjusted under 35 U.S.C. 154(b) by 575 days.

(21) Appl. No.: 10/768,778

(22) Filed: Jan. 30, 2004

(65) Prior Publication Data

US 2005/0171582 A1    Aug. 4, 2005

(51) Int. Cl.
*A61F 7/12* (2006.01)
(52) U.S. Cl. .................................. 607/105; 607/104
(58) Field of Classification Search ............... 606/41, 606/42, 45–50; 607/101–105; 128/898
See application file for complete search history.

(56) References Cited

U.S. PATENT DOCUMENTS

| | | | | |
|---|---|---|---|---|
| 3,298,371 A | * | 1/1967 | Lee | 606/23 |
| 3,948,269 A | * | 4/1976 | Zimmer | 606/24 |
| 5,758,505 A | * | 6/1998 | Dobak et al. | 62/6 |
| 5,769,880 A | * | 6/1998 | Truckai et al. | 607/101 |
| 5,957,920 A | | 9/1999 | Baker | |
| 6,035,238 A | | 3/2000 | Ingle et al. | |
| 6,044,847 A | | 4/2000 | Carter et al. | |
| 6,056,744 A | * | 5/2000 | Edwards | 606/41 |
| 6,081,749 A | | 6/2000 | Ingle et al. | |
| 6,091,995 A | | 7/2000 | Ingle et al. | |
| 6,139,569 A | | 10/2000 | Ingle et al. | |
| 6,156,060 A | | 12/2000 | Roy et al. | |
| 6,197,022 B1 | | 3/2001 | Baker | |
| 6,216,704 B1 | | 4/2001 | Ingle et al. | |
| 6,236,891 B1 | | 5/2001 | Ingle et al. | |
| 6,283,987 B1 | | 9/2001 | Laird et al. | |
| 6,292,700 B1 | | 9/2001 | Morrison et al. | |
| 6,322,584 B2 | | 11/2001 | Ingle et al. | |
| 6,413,255 B1 | | 7/2002 | Stern et al. | |
| 6,416,504 B2 | | 7/2002 | Mosel et al. | |
| 6,461,332 B1 | | 10/2002 | Mosel et al. | |
| 6,480,746 B1 | | 11/2002 | Ingle et al. | |
| 6,524,308 B1 | * | 2/2003 | Muller et al. | 606/49 |

(Continued)

FOREIGN PATENT DOCUMENTS

WO      WO 03/061456 A2      7/2003

(Continued)

OTHER PUBLICATIONS

U.S. Appl. No. 10/759,732, filed Jan. 15, 2004, Mosher et al.

(Continued)

*Primary Examiner*—Roy D Gibson
(74) *Attorney, Agent, or Firm*—Oppenheimer Wolff & Donnelly LLP

(57) ABSTRACT

The present invention provides devices and methods for treating tissue. In one embodiment the present invention provides a method of controlling a temperature of an applicator body, the method comprising providing an applicator body that comprises at least one contact surface A coolant is delivered through at least a portion of the applicator body at a substantially constant rate. Energy is delivered to the coolant through a heating element so that the contact surface of the applicator body is cooled to a desired temperature.

31 Claims, 12 Drawing Sheets

U.S. PATENT DOCUMENTS

| | | |
|---|---|---|
| 6,533,780 B1 | 3/2003 | Laird et al. |
| 6,546,934 B1 | 4/2003 | Ingle et al. |
| 6,572,639 B1 | 6/2003 | Ingle et al. |
| 6,579,266 B2 | 6/2003 | Mosel et al. |
| 6,587,731 B1 | 7/2003 | Ingle et al. |
| 6,685,623 B2 | 2/2004 | Presthus et al. |
| 6,743,165 B2 | 6/2004 | Mosel et al. |
| 6,772,013 B1 | 8/2004 | Ingle et al. |
| 6,776,779 B1 | 8/2004 | Roy et al. |
| 6,830,052 B2 | 12/2004 | Carter et al. |
| 6,836,688 B2 | 12/2004 | Ingle et al. |
| 6,840,954 B2 | 1/2005 | Dietz et al. |
| 6,852,110 B2 | 2/2005 | Roy et al. |
| 2003/0139790 A1 * | 7/2003 | Ingle et al. ............ 607/99 |
| 2003/0144576 A1 | 7/2003 | Presthus et al. |
| 2003/0181965 A1 | 9/2003 | Levy et al. |

FOREIGN PATENT DOCUMENTS

| | | |
|---|---|---|
| WO | WO 03/065915 A1 | 8/2003 |
| WO | WO 03/065916 A1 | 8/2003 |
| WO | WO-03/065917 A1 | 8/2003 |
| WO | WO 03/068095 A1 | 8/2003 |

OTHER PUBLICATIONS

U.S. Appl. No. 10/768,778, filed Jan. 30, 2004, Matlock.
U.S. Appl. No. 10/768,780, filed Jan. 30, 2004, Mosher et al.
U.S. Appl. No. 60/022,790, filed Jul. 30, 1996, Baker.
U.S. Appl. No. 60/024,974, filed Aug. 30, 1996, Baker.

* cited by examiner

ELECTRICALLY HEATED/PHASE CHANGE PROBE TEMPERATURE CONTROL

BACKGROUND OF THE INVENTION

The present invention relates generally to medical devices, methods, and systems. More specifically, the present invention improves the delivery of a therapeutic heating energy that causes tightening, shrinking, and/or debulking of a target tissue, particularly for the noninvasive treatment of urinary incontinence.

Urinary incontinence arises in both women and men with varying degrees of severity, and from different causes. In men, the condition occurs most often as a result of prostatectomies which result in mechanical damage to the sphincter. In women, the condition typically arises after pregnancy where musculoskeletal damage has occurred as a result of inelastic stretching of the structures which support the genitourinary tract. Specifically, pregnancy can result in inelastic stretching of the pelvic floor, the external sphincter, and most often, to the tissue structures which support the bladder and bladder neck region. In each of these cases, urinary leakage typically occurs when a patient's intra-abdominal pressure increases as a result of stress, e.g. coughing, sneezing, laughing, exercise, or the like.

Treatment of urinary incontinence can take a variety of forms. Most simply, the patient can wear absorptive devices or clothing, which is often sufficient for minor leakage events. Alternatively or additionally, patients may undertake exercises intended to strengthen the muscles in the pelvic region, or may attempt behavior modification intended to reduce the incidence of urinary leakage.

In cases where such non-interventional approaches are inadequate or unacceptable, the patient may undergo surgery to correct the problem. A variety of procedures have been developed to correct urinary incontinence in women. Several of these procedures are specifically intended to support the bladder neck region. For example, sutures, straps, or other artificial structures are often looped around the bladder neck and affixed to the pelvis, the endopelvic fascia, the ligaments which support the bladder, or the like. Other procedures involve surgical injections of bulking agents, inflatable balloons, or other elements to mechanically support the bladder neck.

Unfortunately, each of these procedures has associated shortcomings. Surgical operations which involve suturing of the tissue structures supporting the urethra or bladder neck region require great skill and care to achieve the proper level of artificial support. In other words, it is necessary to occlude or support the tissues sufficiently to inhibit urinary leakage, but not so much that intentional voiding is made difficult or impossible. Balloons and other bulking agents which have been inserted can migrate or be absorbed by the body. The presence of such inserts can also be a source of urinary tract infections. Therefore, it would be desirable to provide an improved therapy for urinary incontinence.

One proposed alternative method for treatment of urinary incontinence is described in commonly owned U.S. Pat. No. 6,216,704 B1, the complete disclosure of which is incorporated herein by reference. The proposed method of treating urinary incontinence includes heating and shrinking fascia and other collagenous support tissue in a non-invasive manner to cause the tissue to contract, while minimizing substantial necrosis of adjacent, intermediate tissues. In some embodiments, a plurality of cooled electrodes are used to cool the intermediate tissue and to deliver a therapeutic heating energy to the target tissue.

While the proposed treatment is highly effective, it would be beneficial to better control the temperature of the intermediate tissue that is contacted by the cooled electrodes so as to minimize the damage to the intermediate tissue during delivery of the therapeutic heating energy to the target tissue through the intermediate tissue.

BRIEF SUMMARY OF THE INVENTION

The present invention provides methods, devices, kits, and controllers that control a temperature of a cooled contact surface of an applicator. In one embodiment, the present invention carries out the controlling of the temperature with a phase-change or gas expansion heat exchanger that is positioned within the applicator to control the temperature of electrodes and other portions of a contacting surface of a radio frequency (RF) applicator.

In one aspect, the present invention provides a method of controlling a temperature of an applicator body that is placed in contact with tissue. The method comprises providing an applicator body that comprises at least one contact surface, such as electrode surfaces and insulating surfaces. A coolant is delivered through a conduit in at least a portion of the applicator body adjacent the contact surface at a substantially constant rate. Energy is delivered to the applicator body and/or coolant through one or more heating elements so that the contact surface of the applicator body is cooled to a desired temperature.

In one usage, the contact surface of the applicator is placed against an intermediate tissue that is adjacent a target pelvic support tissue. The cooled contact surface may be placed against the intermediate tissue prior to delivery of a therapeutic energy so as to pre-cool the tissue prior to the heat treatment. A therapeutic heat treatment may be delivered to the target tissue through at least a portion of the contact surface. During such a heat treatment, the cooled contact surface may be held against the intermediate tissue to cool and protect the intermediate tissue.

The coolant flow through the distal portion of the application adjacent the contact surface may cool the contact surface to a temperature between about −5° C. and about 3° C., and preferably about −2° C. Placing the cooled contact surface against the tissue typically cools the contacted intermediate tissue to a temperature between 1° C. and 40° C., and preferably between about 1° C. and 2° C.

One or more temperature sensors may be used to measure one or more temperatures. For example, temperature sensors may be used to measure a temperature of the contact surface during a pre-cooling, of some intermediate interior portion of the applicator, the intermediate tissue during the therapeutic heat treatment, and/or the target tissue. A variety of temperature control algorithms may then be used to effectively control the temperature of the contact surfaces, most of which depend in part on the monitored temperature(s). For example, in one embodiment, a power level of the energy delivered to the heating element is reduced when the therapeutic heating energy is delivered to the one or more electrodes, since the therapeutic heating energy tends to increase the temperature of the contact surface. Even if a therapeutic energy is not delivered to the target tissue, the temperature of the heat exchanger, resistive heater element, edge or interior portions of the applicator or contact surfaces may be monitored and controlled.

If the measured temperature is not at substantially the desired temperature (e.g., within a desired temperature range), the power delivered to the heating element may be adjusted (e.g., raised or lowered) so that the temperature of the contact surface is substantially within the desired cooled temperature range.

In another aspect, the present invention provides an applicator that delivers energy to tissue. The applicator comprises an applicator body that has a proximal portion and a distal portion. A contact surface is disposed on the distal portion of the applicator body. A conduit delivers a coolant on a path through at least a part of the distal portion of the applicator body. One or more heating elements are coupled to the distal portion of the applicator body and are positioned to deliver a heating energy to the coolant in the conduit. The energy delivered to the coolant is sufficient to locally heat the coolant so that the applicator contact surface is at a desired temperature or within a desired temperature range. Typically, the applicator body will be constructed of brass, stainless steel, aluminum, plastics, or a comparable material and will be sized and shaped to access the pelvic support tissues, either transvaginally or laparoscopically.

The delivery device is typically configured to provide a substantially constant flow rate, but if desired the flow rate may be adjusted during the treatment. The flow rate and the energy delivered to the heating element are typically chosen so that the contact surface is held at a temperature between about −5° C. and about 3° C., and preferably about −2° C.

A coolant reservoir may be coupled to an inlet of the conduit to deliver a coolant to the distal portion of the applicator. The coolant reservoir may be coupled to a delivery device, such as a pumping system, which may include mass flow controlling, forward pressure controlling and/or bypass pressure controlling features so as to create a flow of coolant through the conduit through the distal portion of the applicator. Alternatively, the temperature of the coolant in the reservoir may be increased so as to create an increased fluid delivery pressure. The coolant flow rate may be provided at any desired flow rate, but is typically between about 5 and 25 grams per sec., and preferably between about 15 and 20 grams per sec when using R134a material as a coolant.

In embodiments where the flow rate is adjustable, the coolant flow rate may be regulated with a restrictor orifice to control coolant flow to varying flow rates of between one and three different flow rates, depending on whether the applicator is in a pre-treatment stand-by mode, treatment modes, or a post treatment post-cool down mode. These varying flow rates can are controlled with computer controlled, selectable solenoid valves that may be opened individually or in combination to provide these varying flow-rates. As can be appreciated, the valves may be simultaneously closed to prevent coolant flow and completely limit cooling.

A variety of different coolants may be used by the present invention to cool the contact surface to the desired temperature. Some examples include, but are not limited to, RB 276, nitrogen, R152a, R600a, Isobutane, RC270, R420A, R417a, Propane, $CO_2$ and R134a refrigerant, mixtures of various fluids, or similar coolants. The coolant flow rate may be held at a substantially steady rate. Although, as noted above, in alternative embodiments, the fluid flow rate may be adjustable. The coolant may flow from the coolant reservoir and through the fluid conduit that is positioned in a distal portion of the applicator. In one embodiment, the conduit may loop through the distal portion of the applicator. In another embodiment, the fluid conduit may be in the form of a serpentine path so that the coolant is distributed evenly over the contact surface. For example, in one embodiment, coolant is delivered simultaneously into a left and right portion of the distal portion of the applicator and runs through a serpentine path and exits the distal portion through a center conduit.

In one embodiment, the heating element comprises, a resistive heater that is embedded within the distal portion of the applicator. The resistive heater can be any shape and may have a footprint that is larger, smaller or the same size as the heat exchanger footprint. The resistive heater may be energized by a delivery of a current to the resistive heating element. The heating element may be mechanically coupled to a portion of the applicator body so as to deliver heat to the coolant in the distal portion of the applicator. Typically, the power delivered to the resistive heating elements are between about 30 and about 45 watts, but may be higher or lower as desired.

In some embodiments, the applicator may include an array of heating elements that are positioned to create a plurality of heating points. The heating points may provide a same or different level of heating and act to reduce a temperature differential across the contact surface (e.g., electrode surface). The use of an array of heating elements typically reduces a temperature differential across the contact surface to less than 5 degrees Celsius, and preferably below about 1 degree Celsius.

The applicator may include on or within the distal portion of the applicator one or more temperature sensors, such as a thermocouple, thermistor, RTD, infrared sensor, thermal sensing fluid, thermally self-regulating conductive polymer, or thermostatic switching devices. The temperature sensors may be positioned to measure the temperature of at least one of the coolant, a portion of the contact surface, the intermediate tissue, and the target tissue (e.g., a needle-mounted temperature sensor).

The applicator may include or be coupled to a controller that controls the delivery of the coolant flow and the delivery of energy to the internal heating element. The controller may also be used to control the delivery of the therapeutic energy to the target tissue, if desired. The controller typically includes a processor coupled to a memory that stores the code modules that run the computer algorithms and methods of the present invention. The processor of the controller may be in communication with the one or more temperature sensors, the delivery device that controls a flow of the coolant, a power supply coupled to the heating element and/or the heating element (e.g., resistive heating element).

Based at least in part on the temperature signal(s) from the temperature sensor(s), the processor may dynamically adjust the level of energy delivered to the heating element so as to keep the measured temperature of the contact surface within a desired temperature range.

The contact surface may include one or more electrode surfaces and/or electrically insulating surfaces around and/or between the electrode surfaces. A high frequency power source, such as an RF power source, may be coupled to the electrodes so as to deliver a therapeutic energy to the target tissue that is contacted by the contact surface.

In another aspect, the present invention provides a controller for controlling cooling in the applicator. The controller comprises a processor coupled to a memory. The memory is configured to store a plurality of code modules for execution by the processor. The code modules may have stored therein algorithms for controlling the cooling and heating of the target tissue and the intermediate tissue.

In one example, the plurality of code modules may comprise a code module for controlling a delivery of a coolant through a conduit in the applicator, a code module for monitoring a temperature of the contact surface, and a code module for controlling delivery of energy to a heating element that effects a temperature of the coolant adjacent the contact surface. It should be appreciated that the controllers of the present invention may comprise any combination of modules and the present invention is not limited to the code modules listed.

In a further aspect, the present invention provides kits. The kits may include any of the applicators or probes described herein. The kits may further include instructions for use setting forth any of the methods described herein. The kits may also include packaging suitable for containing the applicator and the instructions for use. Exemplary packaging include pouches, trays, boxes, tubes, and the like. The instructions for use may be provided on a separate sheet of paper or other medium. Optionally, the instructions may be printed in whole or in part on the packaging. Usually, at least the distal portion of the applicator will be provided in a sterilized condition. Other kit components, such as a high frequency power supply (RF) and a controller may also be included.

These and other aspects of the invention will become more apparent from the following detailed description of the invention when taken in conjunction with the accompanying exemplary drawings.

DETAILED DESCRIPTION OF THE INVENTION

Figure 1:
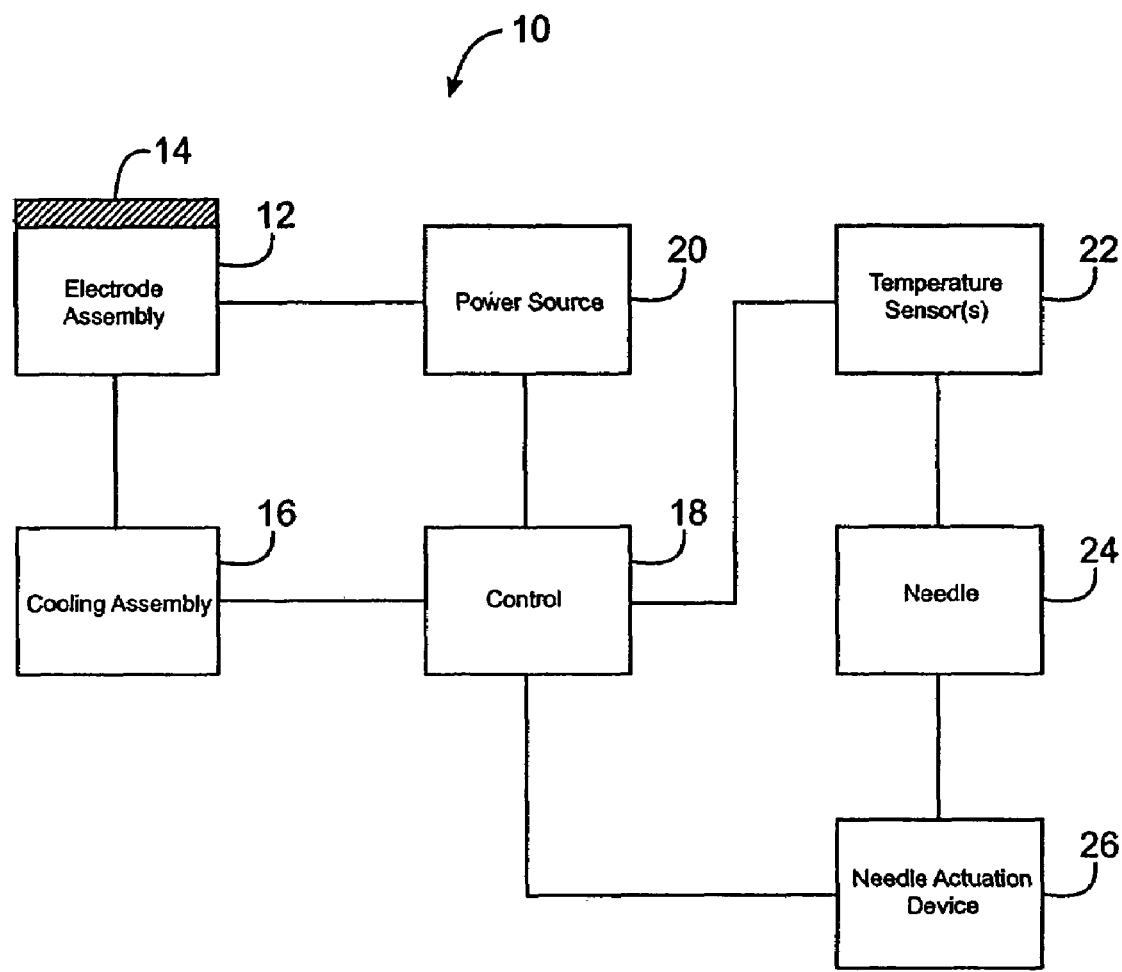
FIG. 1 schematically illustrates a system incorporating the present invention.

The present invention provides methods, devices, systems, controllers, and software algorithms for controlling a temperature of a tissue contacted by a surface of an applicator during delivery of a therapeutic energy to an underlying support tissue. The present invention may enhance the structural support provided by the support tissues by inducing controlled stiffening, contraction, or shrinkage of the structural support tissue, which are typically a collagenous tissue such as fascia, ligament, or the like.

In one specific use, the present invention is for treatment of urinary incontinence. The structural support tissue will typically be part of a pelvic support system that is responsible in some manner for control of urination, or for supporting such a tissue. The tissues of the pelvic support system generally maintain the position of the genitourinary tract, and particularly the position of urinary bladder, urethra, and the bladder neck coupling these structures.

For treatment of urinary incontinence, the present invention relates to improving the controlled shrinkage or contraction of an endopelvic fascia or other related collagenated tissue. In general, endopelvic fascia may define a hammock-like structure, which extends laterally between the left and right arcus tendineus fasciae pelvis (ATFP). These tendon structures may extend substantially between the anterior and posterior portions of the pelvis, so that the endopelvic fascia EF at least partially defines the pelvic floor.

The fascial tissue of the pelvic support system may comprise tissues referred to under different names by surgeons of different disciplines, and possibly even by different practitioners within a specialty. In fact, some surgeons may assign a collagenous support structure of the endopelvic fascia one name when viewed from a superior approach, and a different name when viewed from an inferior approach. Some of the endopelvic fascia may comprise two collagenous layers with a thin muscular layer there between, or may comprise a single collagenous layer. The hammock-like endopelvic fascia described herein may be damaged or missing, particularly after pregnancy, so that the support of the genitourinary tract is instead provided by a variety of fascial layers, muscular tissues, ligaments, and/or tendons within the pelvis.

Hence, the treatment of the present invention may be directed at a variety of tissue structures defining the pelvic floor and/or diaphragm including, but not limited to the ureter, the sphincter, pelvic ligaments, pelvic floor muscles, a suspension ligament (such as the anterior sacro-coccygeal ligament); arcus tendineus fasciae pelvis ATFP, the white line of the pelvis; fasciae of the obturator internus muscle; the arcus tendineus levator ani or "picket fence" to the iliococcygeus portion of the levator ani muscle; bulbocavernosus muscle; ischiocavernosus muscle; urethrovaginal sphincter; m. compressor urethrae muscle; and m. sphincter urethrovaginal muscle which replaces deep perineal muscle); structures of the bladder and urethra (including but not limited to: urethral wall; urethrovesical fascia; bladder suspension ligaments; detrusor muscle; bladder neck; and the pubococcygeus muscle which relaxes to open the bladder neck, initiating micturation); structures of the vagina (including: vagino-uterine fascia, lamina propria—the dense connective tissue layer just under the epithelium; pubo-urethral or pubo-prostatic ligaments; pubo-vesicle ligament and posterior pubo-urethral or puboprostatic ligament; pubovesicle muscle, a smooth muscle that is integrated with the pubovesicle ligament; and pubocervical fascia which attaches to the ATFP); structures of the uterus (including: round ligament; sacrouterine ligament; and broad ligament); and structures of the bowel (including: rectal fascia and mackenrodt's ligament).

When the endopelvic fascia has excessive length or stretches excessively under a load, the fluid pressure within the bladder advances into the bladder neck and down the urethra more readily. Leakage may result in part because the endopelvic fascia allows the bladder, bladder neck, and/or urethra to drop below its desired position, at which fluid pressure within the bladder may actually help to seal the bladder neck. Stretching of the endopelvic fascia may also alter the timing of pressure pulse transmission to the urethra.

When a continent woman coughs, the pressure in the urethra will often increase more than one-tenth of a second prior to the increase in bladder pressure. In women with stress incontinence, the bladder pressure may rise first. For a continent woman having endopelvic fascia which stretches much less under the influence of a pressure pulse, the time delay between initiation of the pressure pulse and transferring sufficient force to the urethra to effect closure may therefore be significantly less. By treating the endopelvic fascia to decrease its length and/or increase its stiffness, the descent time of the pelvic viscera during a cough will be shorter than an untreated, excessively long and/or excessively elastic tissue.

The support tissue may be treated non-surgically or it may be accessed for direct treatment in a variety of ways. For example, the surface of the endopelvic fascia (or other tissue) may be accessed transvaginally by forming and displacing a flap from the vaginal wall with the assistance of a weighted speculum. Alternatively, the endopelvic fascia may be accessed laparoscopically.

Tissue contraction or stiffening results from controlled heating of the tissue by affecting the collagen molecules of the tissue. Contraction occurs as a result of heat-induced uncoiling and repositioning of the collagen β-pleated structure. By maintaining the times and temperatures set forth below, significant tissue contraction can be achieved without substantial collateral tissue necrosis. Stiffening results from the loss of elasticity of the tissue due to the formation of scar tissue and/or attachment of adjacent support tissues to each other as a result of controlled heating of the tissue.

The temperature of the target tissue structure will generally be raised to a temperature in the range from about 60° C. to about 110° C., often being in the range from about 60° C. to about 80° C., preferably in the range from about 65° C. to about 75° C., and more preferably from about 69° C. to about 75° C. Such heating will generally be carried out for a period from about 30 seconds to about 5 minutes. These heating times will vary depending on the configuration of the electrodes, power source, target tissue, and the like. One exemplary method of controlling heating of the tissue is described in co-pending U.S. patent application Ser. No. 10/102,596, filed Mar. 19, 2002, the complete disclosure of which is incorporated herein by reference.

The heating may effect a shrinkage of the target tissue in at least one dimension of between about 15 percent and 50 percent, and preferably at least about 40 percent. Alternatively, the temperature of the target tissue structure will generally be raised to value in the range of about 45° C. to about 60° C. and will generally effect stiffening of the target tissue. The rise in temperature may be quite fast, although there will often be advantages in heating tissues more slowly, as this will allow sufficient heat to be removed from tissues which are not targeted for therapy, thereby minimizing collateral damage. However, if too little heating energy is absorbed by the tissue, blood perfusion will transfer the heat away from the targeted tissue, so that the temperature will not rise sufficiently to effect therapy.

The total amount of energy delivered will depend in part on which tissue structure is being treated, how much tissue is disposed between the target tissue and the heating electrode (s), and the specific temperature and time selected for the protocol. The power delivered will often be in the range from about 2 W to about 100 W, usually being about 2 W to about 50 W, and preferably between about 12 W and 40 W. For example, in one embodiment, the power is delivered in a range of about 12 W to about 15 W. During dwell (e.g., maintaining the tissue temperature above a target temperature for a desired time period), the power may be varied. In one exemplary treatment program, the power may initially be delivered in a range of about 15 W to about 20 W for a first time period, and thereafter delivered in a range of about 30 W to about 40 W for a second time period. During dwell, the power may be varied by ±0 W to ±10 W from the power level in the second time period so as to maintain the tissue temperature at a target temperature. The temperature will usually not drop instantaneously when the heating energy stops, so that the tissue may remain at or near the therapy temperature for a time from about 10 seconds to about 2 minutes, and will often cool gradually back to body temperature.

While the remaining description is generally directed to a system for treatment of urinary stress incontinence of a female patient, it will be appreciated that the present invention will find many other applications for selectively directing therapeutic heating energy into the tissues of a patient body. For example, treatment of other conditions may be effected by selective ablation, shrinking or stiffening of a wide variety of other tissues, including (but not limited to) the diaphragm, the abdominal wall, the breast supporting ligaments, the fascia and ligaments of the joints, the collagenous tissues of the skin, tumors, and the like.

Figure 2:
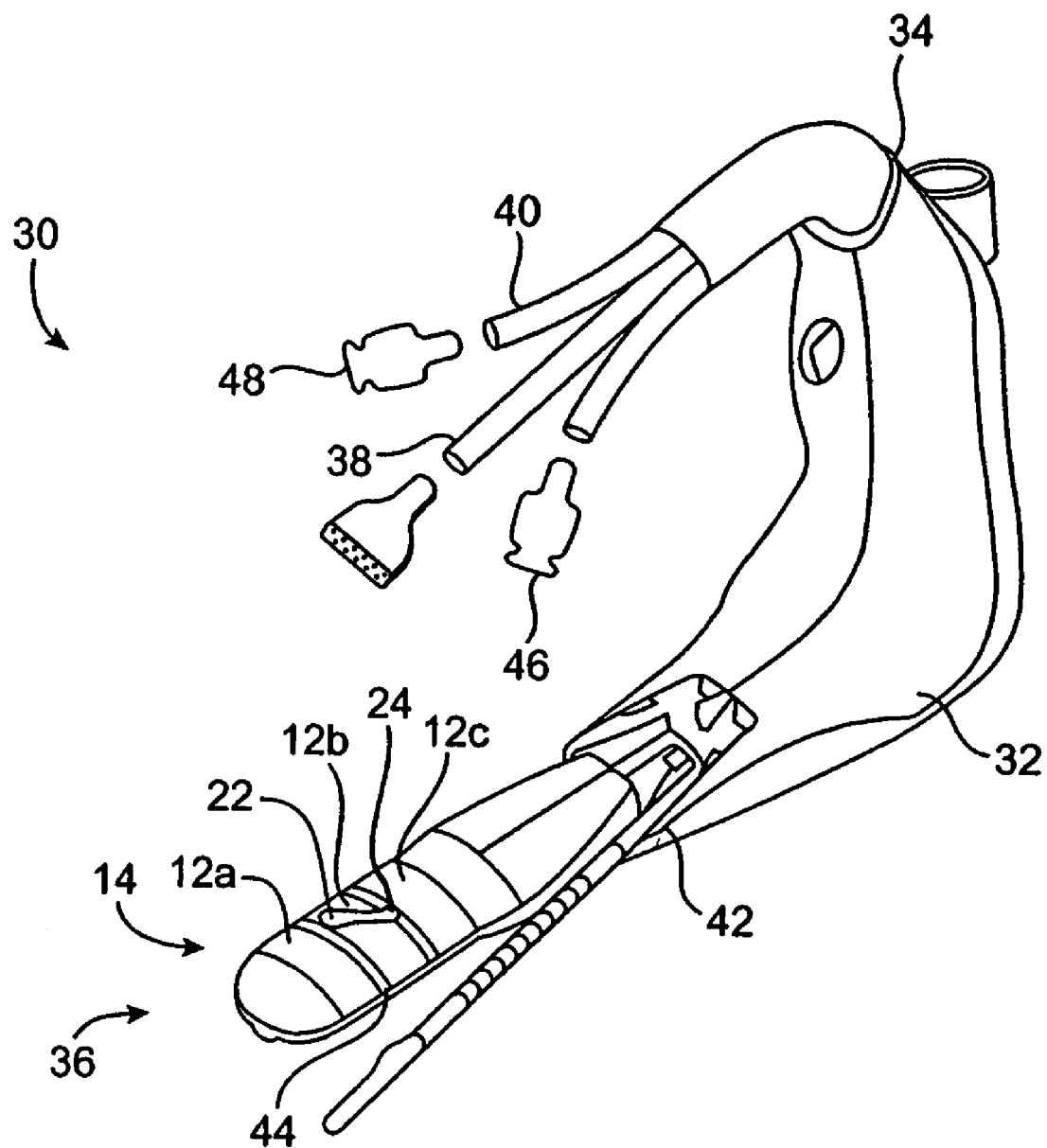
FIG. 2 is a perspective view of a simplified applicator encompassed by the present invention.

FIG. 1 schematically illustrates a simplified system 10 of the present invention. System 10 includes a tissue contacting surface 14 that includes at least in part a surface of electrode assembly 12 and spacers 44 around and/or between electrode assembly 12 (FIG. 2). Electrode assembly 12 can include one or more individual electrodes and may be positioned on a distal portion of an applicator body 32 (FIG. 2). System 10 may include a cooling assembly 16 that is in part positioned adjacent contact surface 14 so as to cool the tissue contacting surface 14 to a desired cooled temperature. A control 18 may be coupled to a power source 20, cooling assembly 16, and electrode assembly 12 to control the therapeutic heating and cooling therapy. Control 18 may comprise one or more processors and a memory for storing the software algorithms that are implemented by the present invention.

System 10 may optionally include one or more temperature sensor(s) 22 that are coupled to control 18. Temperature sensor(s) 22 may be attached to the applicator body and include one or more discrete temperature sensors, such as a thermocouple, that may be used to monitor a temperature of the intermediate tissue, target tissue, and/or contacting surface 14. In other embodiments, however, temperature sensor 22 may be part of an assembly that is separate from the applicator body.

In exemplary embodiments, at least one temperature sensor 22 may be positioned on a needle 24, such as a nitinol, stainless steel, composite, or polymer needle, that is deployable from the applicator body. If temperature sensor 22 is attached to needle 24, system 10 may include a needle deployment device 26 to deploy the needle from a retracted position to a deployed position. Additionally or alternatively, temperature sensor(s) 22 can be attached directly to the applicator body so as to measure the temperature of the surface of the intermediate tissue and/or to monitor a temperature of the electrode surface. A complete description of one suitable temperature sensor is described in co-pending and commonly owned U.S. patent application Ser. No. 10/211,973, filed Aug. 1, 2002, the complete disclosure of which is incorporated herein by reference.

FIG. 2 illustrates one exemplary applicator 30 of the present invention that is used to deliver the therapeutic energy to the target tissue. The applicator 30 generally includes an applicator body 32 having a proximal portion 34 (e.g., handle) and a distal portion 36 (e.g., applicator tip). Electrode assembly 12 may include a plurality of electrodes 12a, 12b, 12c attached to the distal portion 36 of applicator body 32 to deliver a therapeutic energy to the target tissue. In the illustrated embodiment, there are three electrodes 12a, 12b, 12c that may be coupled to a power source, such as a high frequency power source (e.g., RF energy, microwave or the like). The power source may be connected to control 18 (FIG. 1) through connector 38. It should be appreciated, however, that for ease of illustration three electrodes and one connector 38 are illustrated. However, the applicators 30 of the present invention may include any number of electrodes and connectors.

In some embodiments, applicator 30 may optionally include a guide assembly 42 to assist in positioning electrodes 12 adjacent the target tissue within the patient's body. A more complete description of guide assembly 42 may be found in co-pending and commonly owned U.S. patent application Ser. No. 09/991,368, filed Nov. 20, 2001 and U.S. patent application Ser. No. 10/301,561, filed on Nov. 20, 2002, the complete disclosures of which are incorporated herein by reference.

Applicator body 32 may also carry needle 24 for deployment into the patient's tissue. Needle 24 typically carries one or more temperature sensors 22. It should be appreciated, however, that needle 24 may carry an electrode, and/or the needle may be used for delivering a medicant, pharmacological agents, saline, fluids to enhance energy delivery, or the like. A more complete description of some exemplary applicators that can carry the needle 24 of the present invention are described in commonly owned U.S. Pat. Nos. 6,035,238, 6,044,847, 6,091,995, 6,156,060, 6,139,569, 6,216,704, 6,236,891, 6,283,987, and 6,292,700, the complete disclosures of which are incorporated herein by reference.

Electrode assembly 12 of the present invention will generally include a series of conductive surface segments which are aligned to define a substantially planar electrode surface. The electrode surface segments may be separated by an electrically insulating material 44, with the insulation being much smaller in surface area than the conductive segments. Typically, there will be between one and eight electrodes, which are separated by a distance of between about 1 mm and 10.0 mm with the preferred spacing of about 6 mm. Alternatively, the electrodes may be conductive areas on a flexible printed circuit assembly which are mounted on an insulating substrate. The substrate may be attached to the applicator body by pressure sensitive or thermo-set adhesives. This embodiment eliminates the costs and manufacturing difficulties associated with discrete insulating segments between the electrodes.

In some embodiments, electrodes 12 may be rounded and/or covered by an insulating material to prevent concentrations of the electrical potential and injury to the engaged tissue surfaces.

In the embodiment illustrated in FIG. 2, electrode assembly 12 includes electrodes 12a, 12b, 12c, each of which is electrically isolated from the other electrodes through an electrically insulating and thermally conductive space 44. This allows each of the electrodes to be individually energized so as to selectively deliver heating energy to a specific portion of the target tissue. Electrodes 12a, 12b, and 12c may comprise surfaces of separated segments of metalized or plated ceramic, metalized or plated polymer, electrically conductive polymer, plated aluminum, gold plated brass, gold plated copper, stainless steel, sintered metal, or the like.

It should also be understood that while electrode assembly 12 of the present invention is generally herein described with reference to a linear array geometry, the present invention also encompasses electrodes which are segmented into two-dimensional arrays, electrodes that are rotatable, non-linear electrode assemblies, curved electrodes, ribbed electrodes, electrodes positioned on a needle array, or the like. A more detailed description of a needle electrode array is described in U.S. Provisional Application No. 60/440,711, filed Jan. 16, 2003, the complete disclosure of which is incorporated herein by reference. Where opposed sides of the tissue are accessible for relatively large array structures, such as along the exposed skin, or near the major cavities and orifices of the body, the electrode surfaces will preferably be separated by a gap which is less than a width (and length) of the electrodes.

For example, in some embodiments, one electrode structure may be disposed within a large body cavity such as the rectum or vagina, while the other is placed in an adjacent cavity, or on the skin so that the region to be treated is between the electrode surfaces. In other embodiments, one or both electrodes may be inserted and positioned laparoscopically. It will often be desirable to clamp the tissue tightly between the electrodes to minimize the gap therebetween, and to promote efficient coupling of the electrode to the tissue.

In exemplary embodiments, electrodes 12a, 12b, 12c, are energized by a radiofrequency (RF) power source 20. Multiplexers (not shown) may be used with control 18 to individually energize each electrode, typically varying the power or time each segment is energized to more nearly uniformly heat fascia or other target tissue. The use of a radiofrequency current of relatively low voltage, helps to avoid arcing and damage to the intermediate tissue in direct contact with electrodes 12. Generally, sufficient heating can be provided by a current of between about 0.2 amps and 2.0 amps, preferably about 1.0 amp, and a maximum voltage of between about 30 and 100 volts rms., preferably being about 60 volts rms. Each electrode will often have a surface area of between about 0.5 cm$^2$ and 200 cm$^2$, and the current density in the target tissue will often be between about 1 mA/cm$^2$ and 4 A/cm$^2$, preferably being between about 5 mA/cm$^2$ and 500 mA/cm$^2$. This can provide a maximum power in the range from about 10 W to about 200 W, often being about 30 W. Using such low power settings, if electrode 12 is lifted away from the intermediate tissue, there will typically be no arcing. Instead, the current will simply stop. This highlights the difference between the electrical tissue heating of the present invention and other conventional electrosurgical techniques. Some exemplary heating methods are described in commonly owned U.S. patent application Ser. No. 10/102,596, filed Mar. 19, 2002, and U.S. patent application Ser. No. 10/768,780, entitled "Heating Method for Tissue Contraction," filed concurrently herewith, and U.S. patent application Ser. No. 10/759,732, entitled, "Non-Surgical Incontinence Treatment System and Method," filed on Jan. 15, 2004, the complete disclosures of which are incorporated herein by reference.

To selectively heat a target tissue while reducing the amount of necrosis to the tissue between the target tissue and the electrodes (e.g., intermediate tissue), contacting surfaces 14 of the applicator, such as electrode surface and other insulating surfaces on the distal portion of the applicator 30 may be cooled with cooling assembly 16 (FIG. 1), such as a phase-change heat exchanger that is disposed within the applicator.

Figure 3:
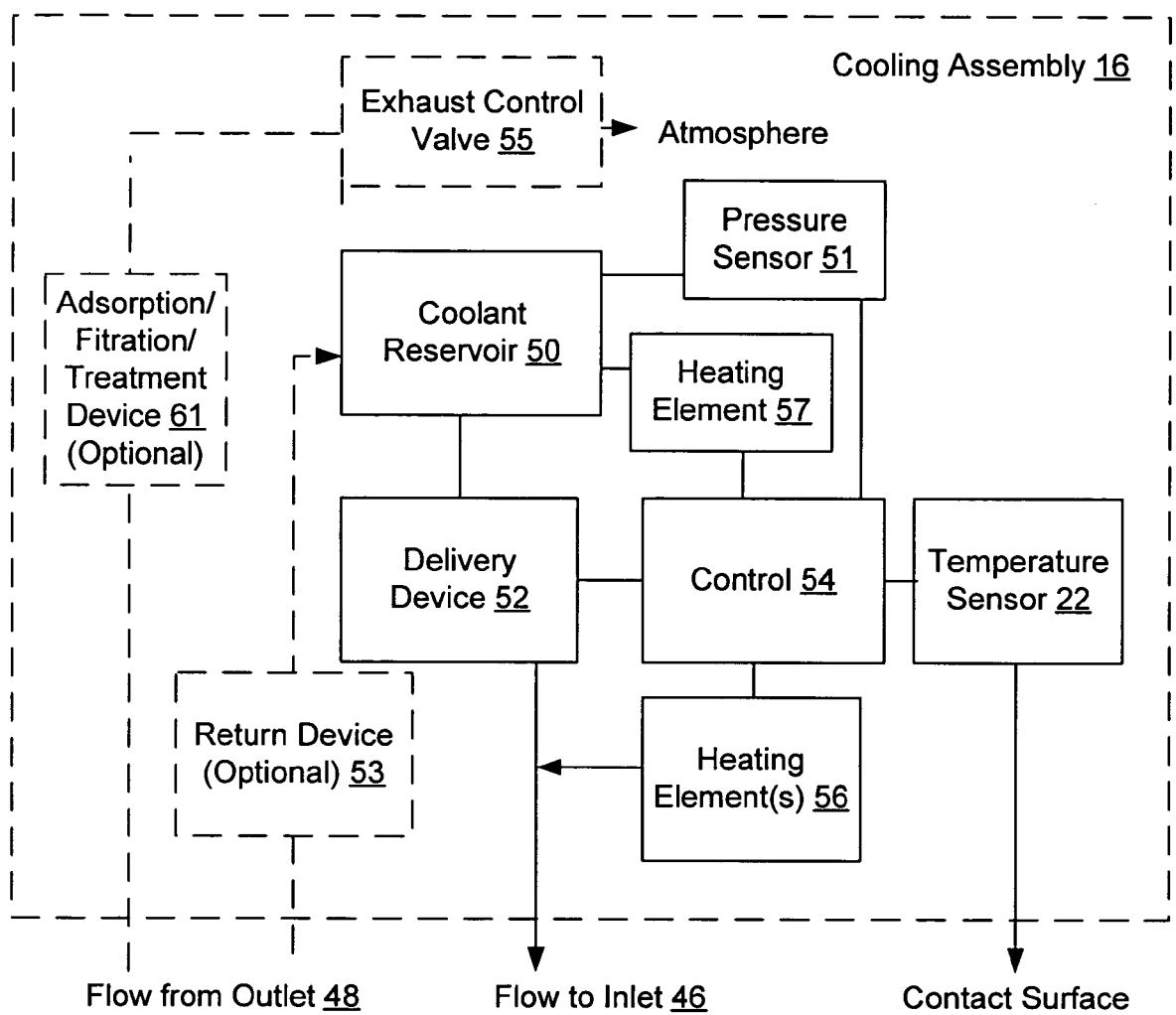
FIG. 3 schematically illustrates a cooling assembly encompassed by the present invention.

FIG. 3 schematically illustrates one cooling assembly 16 that is encompassed by the present invention. As can be appreciated, the cooling assembly of FIG. 3 is merely an example, and other cooling systems that have more or less elements are also encompassed by the present invention. Cooling assembly 16 typically cools an area which extends beyond the energized electrode surface to prevent the formation of any hot spots adjacent the tissue surface, and to maximize the heat removal from intermediate tissue without chilling it to or below temperatures that irreversibly damages the tissue, such as might occur when freezing the tissue.

Cooling assembly 16 may include a coolant reservoir 50 coupled to a conduit 40 which extends through the distal portion 36 of the applicator. Cooling assembly may optionally include a coolant delivery device 52 that assists in delivering the coolant into the distal portion of the applicator and/or a return device 53 to assist in returning the coolant from the distal portion 36 back to reservoir 50. Delivery device 52 is typically in the form of a rotary pump, such as the Tuthill Corporation volumetric gear pump (12 vdc, 0.1 CC per revolution), vane, and the like. A return device 53 are typically in the form of a Tecumseh refrigeration compressor (AEA Series), diaphragm, or piston pump and the like.

Instead of using pumps to control the delivery and return of the coolant, a preferred embodiment of the present invention uses the fact that the temperature of the reservoir determines the pressure of the cooling fluid. By raising the temperature of the cooling fluid in the reservoir 50 slightly, sufficient pressure may be achieved to reliably deliver the coolant to the applicator without the need for delivery device 52. For example, when using R134 at room temperature (between about 18° C.-24° C.) typical fluid delivery pressure is between about 65 psi to about 75 psi. Increasing the reservoir temperature to between about 40° C. to 45° C. raises the delivery pressure to between about 90 psi to about 95 psi and ensure that the R134a material remains in liquid form all the way to the applicator. Upon reaching the applicator, the R134a begins to transition to the gas phase. This occurs only when it moves from the delivery conduit out into a channel within the distal portion of the applicator. In embodiments where a compressor return device is used may lead to formation of some gas on the inlet side of the compressor which may lead to periodic variations in the gas flow rate which adversely affect the temperature stability of the coolant, and hence the temperature stability of the contact surface.

Coolant delivery device 52 or the temperature of the reservoir may be controlled by control 54 or by master control 18 (FIG. 1). The control of reservoir temperature or pump speed may be achieved by adding a pressure sensor 51 which allows the control 54 to monitor pressure and adjust the amount of power delivered to strip heating elements 57 mounted on the side of the reservoir 50. Alternately the reservoir may be placed within a closed oven like chamber whose temperature is regulated to achieve the desired delivery pressure. A weir-style bottom draining vapor/liquid separation device may be employed down-stream from the pumping devices to provide, to the applicator body a substantially higher percentage of liquid. One or more temperature sensors 22 may be coupled to control 54 and positioned adjacent the contact surface 14 of applicator 30 to measure the temperature of the contact surface 14 and/or the intermediate tissue. As will be described below, if the measured temperature of the contact surface is too high or too low, one or more heating elements 56 may be activated or deactivated by control 54 so that the temperature of the contact surface/intermediate tissue is within a desired temperature range. Alternatively or additionally, one or more temperature sensors, such as a thermocouple (not shown), may be attached to a deployable needle and may also be in communication with control 54 so as to provide temperature information about the target tissue.

A variety of different coolants for circulation through conduit 40 in applicator 30 may be used with the present invention. The selected coolant should be non toxic and should provide an efficient cooling effect at low flow rates. Some coolants that are suitable for use in applicator 30, include, but are not limited to, RB 276, nitrogen, R420A, R417a, propane, $CO_2$, R134a refrigerant, mixtures of various other coolants, fluids, and the like.

As shown in FIG. 2, conduit 40 defines a flow path between a cooling inflow port 46 and a cooling outflow port 48, in which coolant from reservoir 50 and delivery device 52 is cycled through applicator 30 and returned to the coolant reservoir 50 using an optional return device 53. Alternatively, as shown in FIG. 3, the returning coolant may flow through outflow port 48 and/or be optionally treated through an adsorption, filtration and/or catalytic system 61, and thereafter be allowed to escape to the atmosphere, within the control system through an exhaust control valve 55.

The coolant flow rate may be chosen to be substantially constant, or the coolant flow rate may be chosen to be variable during the therapeutic treatment. While a temperature of the contact surface may be monitored and the coolant flow rate may be varied to compensate for the temperature fluctuations at the contact surface, Applicants have found that a delivery device provides a substantially constant coolant flow rate (with local heating of the coolant at the distal portion of applicator 30 using one or more heating elements 56) achieves superior cooling for a number of reasons. For example, the local heating of a constant flowing coolant using a local heating element provides (1) a solid state heating element that results in increased reliability versus a mechanical valve, (2) the solid state heating element requires less volume and is noiseless (versus an audible clicking of the valve, (3) provides a more rapid response of a "locally" controlled heat exchange via a resistive heating element than a remotely controlled valve which is as far away as 5' to 10', (4) the local heating element induces a temperature variation in the cooling chamber in as quickly as 0.5 second whereas a remote valve changing coolant flow rate would result in 5 to 20 seconds of control delay due to the extremely low coolant flow rates, and (5) the local heating element(s) 56 reduce temperature distribution variations across the applicator.

To heat the heat exchanger body and flowing coolant so that the temperature of the contact surface 14 and/or the intermediate tissue is within a desired range, one or more local heating elements 56 are coupled to the distal portion 36 of the applicator body 32. Heating element 56 may be coupled to a power source through one or more connector wires 60. A power between about 30 watts and about 45 watts may be delivered over connector wires 60 to energize the heating element 56. The heating element(s) 56 are typically attached to the applicator body opposite of the contact surface (e.g., bottom surface) or positioned in a slot on the applicator body. For example, as shown in FIGS. 4A, 4B, 4D, 4E, and 4F, a single embedded resistive heating element, or the like may be used to locally heat the distal portion 36 of applicator 30 and the returning coolant. The heating element 56 may be any shape and size, but is typically a flat profile power resistor. In one embodiment, the heating element is a power film resistor, such as the Caddock mp725 or Caddock mp850, which delivers a power of 40 watts at 36 volts.

Applicants have found that strategically positioning one or more heating elements 56 on the distal portion 36 may reduce the temperature differential across the contact surface. FIGS. 4D, 4E, and 4F illustrate some useful examples of a placement of the heating element(s) 56 on or within the distal portion 36 of applicator body 32 which balance a temperature variation across the applicator body that is caused by the flow pattern of the coolant.

In its simplest form, as shown in FIGS. 4E, a single resistive heating element 56 may be symmetrically mounted about a center point 59 beneath the contact surface 14 (e.g., electrode surface and insulator surfaces) of the distal portion 36 of applicator body 32. In such a configuration, Applicants have found that, a temperature variation on the contact surface will be about 5 degrees Celsius or less.

Since the coolant enters distal portion 36 of the applicator body from one side (typically proximal side 31), the greatest cooling effect is typically found at the proximal side 31 of the distal portion 36 where the coolant enters. Thus, by moving the heating element 56 towards the proximal side 31, a significant improvement in the temperature variation across the applicator contact surface 14 may be achieved. For example, in the embodiment of FIG. 4F, the heating element 56 may be mounted "off-center" of a middle point 59 of the contact surface 14 of distal portion 36 in the applicator body 32. In the illustrated embodiment, the contact surface is about 30 mm long and the heating element 56 was moved proximally about 3 mm off the center point 59. Such an embodiment reduces the temperature variation across the contact surface to less than about 2 degrees Celsius.

As can be appreciated, the present invention is not limited to only one heating element 56. An array of small wattage heating elements 56 may be positioned in such a way as to reduce the spatial temperature distribution across the applicator body contact surface as a result of coolant flow through the applicator. FIGS. 4G to 4I illustrate some illustrative examples of an array of resistive heating elements 56 that may be used with the applicators 30 of the present invention.

In one configuration shown in FIG. 4G, an array of two resistive heating elements 56, 56' are positioned beneath the contact surface 14 in the distal portion 36 of the applicator body 32 so as to evenly distribute heat and reduce the temperature variation across the contact surface. Some useful resistive heating elements are the Caddock mp821 series which can deliver 20 watts at 14 volts across each 10 Ω resistive heating element. The resistive heating elements 56, 56' may be evenly spaced about a center point 59 of the contact surface or heating elements 56, 56' may be mounted off centered about center point 59 so as to provide more even cooling across the contact surface. For example, as illustrated in FIG. 4G, for a distal portion having a length of 30.0 mm and width of 25.0 mm, heating element 56' is mounted about 1.5 mm farther from the center point 59 than heating element 56. In such an embodiment, the temperature variation may be reduced to 1 degree Celsius or less.

However, instead of moving heating element 56' to an off-centered position, it may be possible to provide a resistance differential between heating elements 56, 56' so that there is more heating adjacent the proximal end 31. Moreover, each of heating elements 56, 56' may be coupled to a same or different power source and may deliver the same heat or different heat. If heating elements 56, 56' provide different heat, heating element 56' will typically deliver more heat so as to better counter the greater cooling effect at the entry point of the coolant.

In another configuration shown in FIG. 4H, an eight resistor array of 5 watt power resistors may be spaced within the distal portion 36 of applicator body 32 to permit a plurality of heating points so as to further reduce the spatial temperature distribution across the contact surface. Applicants have found that by distributing a plurality of heating elements 56 through the applicator body 32, the temperature variation may be reduced to less than about 1 degree Celsius to about 2 degrees Celsius.

When the array of heating elements 56 is used, each of the heating elements 56 may be configured to have the same wattage (e.g., 5 W) or the resistors could be configured to have different wattages. In the illustrated embodiment of FIG. 4H, the heating elements R1, R2, . . . R8 are coupled in series to a single power source. The heating elements may have different resistance values so as to deliver a differential heating to the different portions of the distal portion 36. For example, R1 and R2 may have a resistance value of 2.0 Ω, R3-R6 may have a resistance value of 2.5 Ω, and R7 and R8 may have a resistance value of 3 Ω. In the illustrated configuration, the distal portion 36 has a length of about 30.0 mm and the heating elements are about 5 mm wide by 10 mm long. Such a configuration provides a common excitation voltage while providing a tailored heating profile to compensate for the natural heat distribution across the distal portion 36.

As shown in FIG. 4I, instead of positioning all of the resistive heating elements along a longitudinal axis of the distal portion 36 of body 32, the resistive heating elements may be positioned in a serpentine configuration such that R1, R2, . . . R9 are strategically dispersed over the distal portion. In the configuration of FIG. 4I, a constant voltage is applied and different resistance values are provided in the heating elements to cause the variable heating profile. One useful example has R1, R2, and R3 with a resistance value of 2 Ω, R4, R5, and R6 with a resistance value of 2.5 Ω, and R6, R7, and R8 with a resistance value of 3 Ω. As can be appreciated, such a configuration provides greater local heating adjacent proximal end 31 so as to better counter the greater cooling effect at the entry point of the coolant.

It should be appreciated that the embodiments of FIGS. 4A to 4I are merely illustrative and should not limit the scope of the present invention. The present invention may use as many heating elements as desired and may use a variety of different resistance values to provide different heating energy.

Figure 4A:
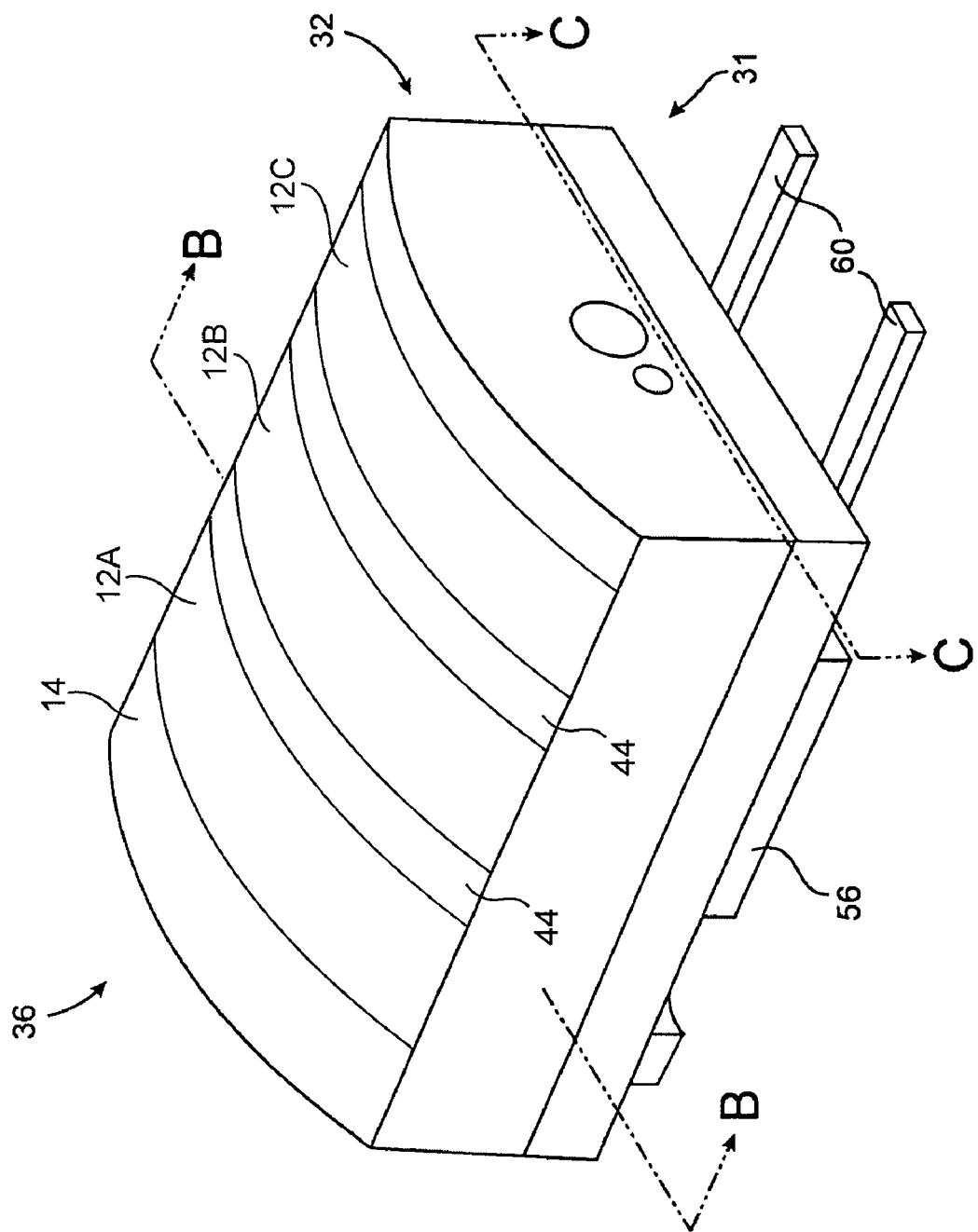
FIGS. 4A and 4D illustrate a heating element coupled to a distal portion of the applicator of FIG. 2.
Figure 4B:
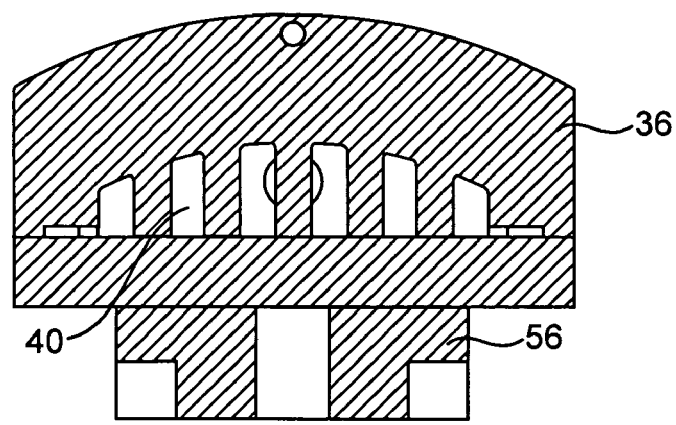
FIGS. 4B and 4C are cross sectional views of the flow conduit along lines B-B and C-C.
Figure 4C:
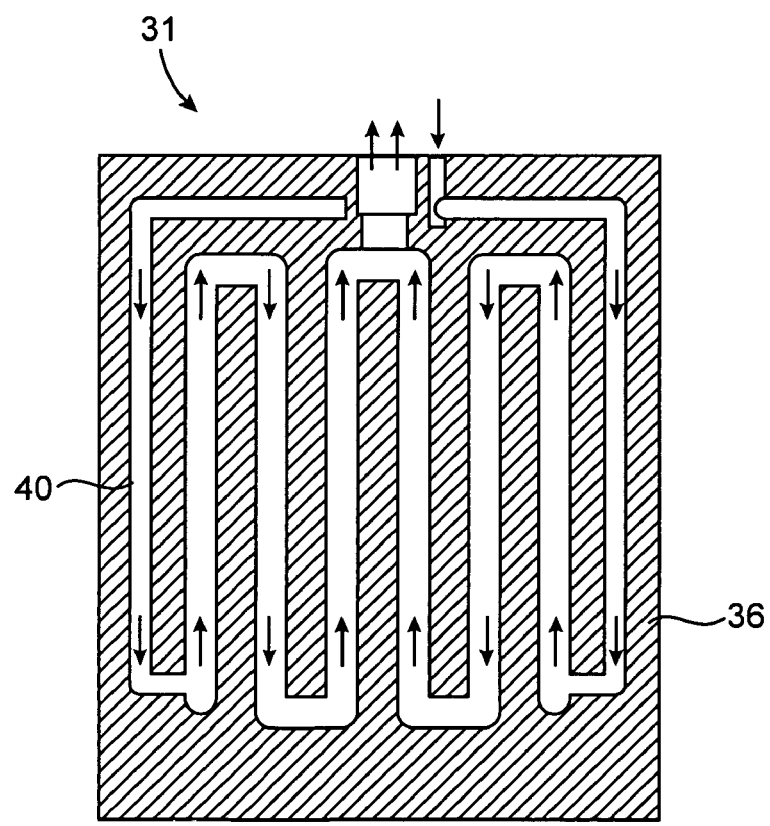
Figure 4D:
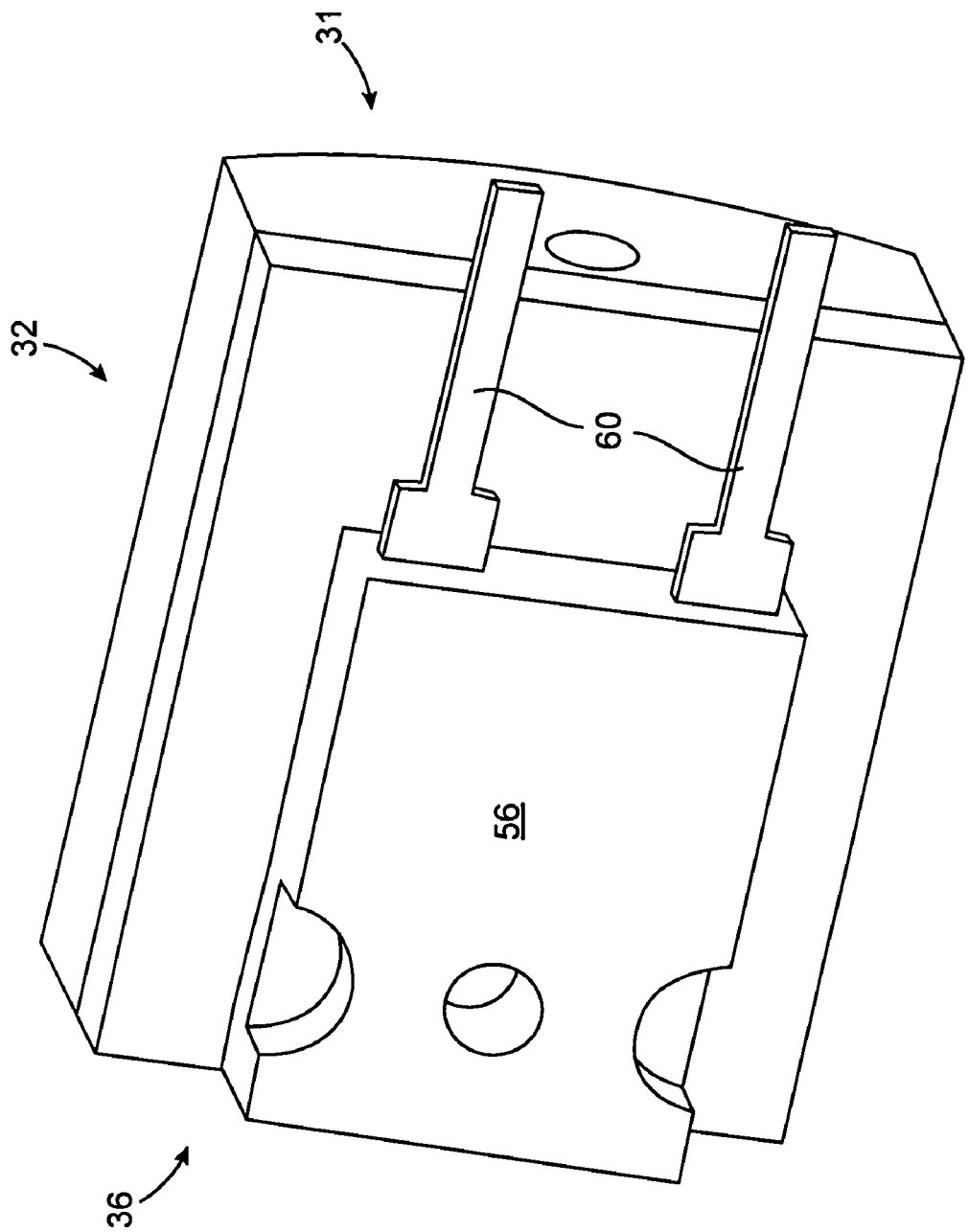
Figure 4E:
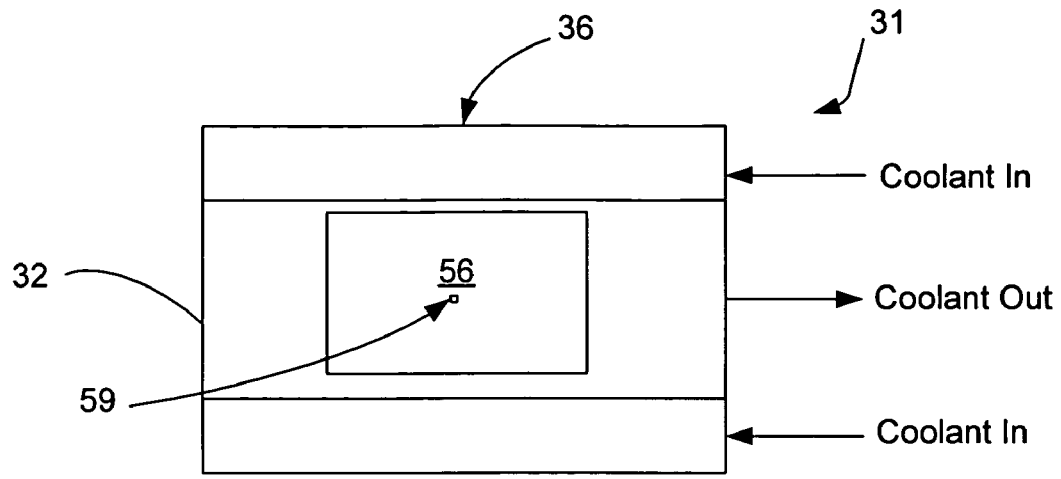
FIGS. 4E to 4I illustrate a variety of different positions of the heating element(s) on the applicator.
Figure 4F:
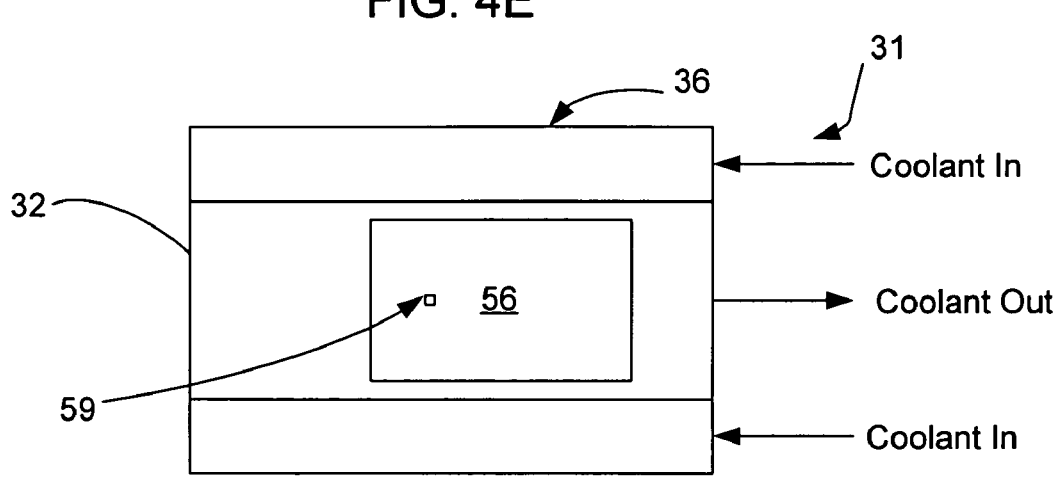
Figure 4G:
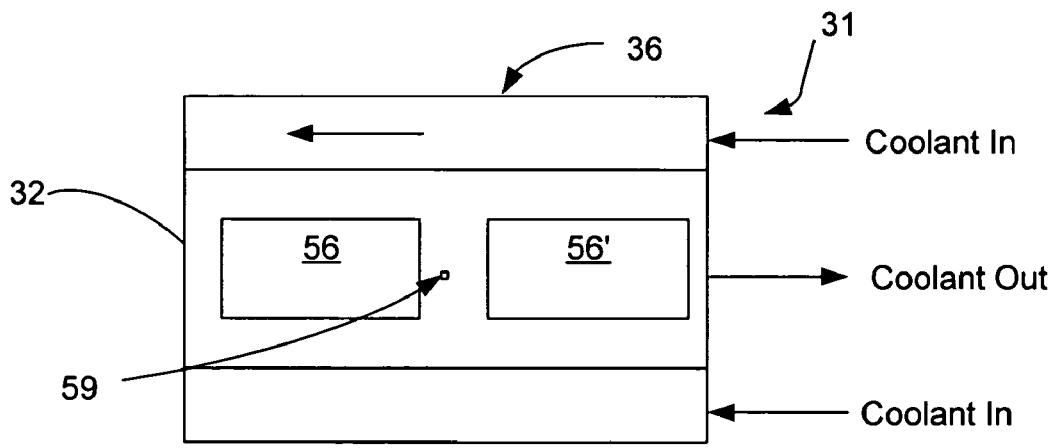
Figure 4H:
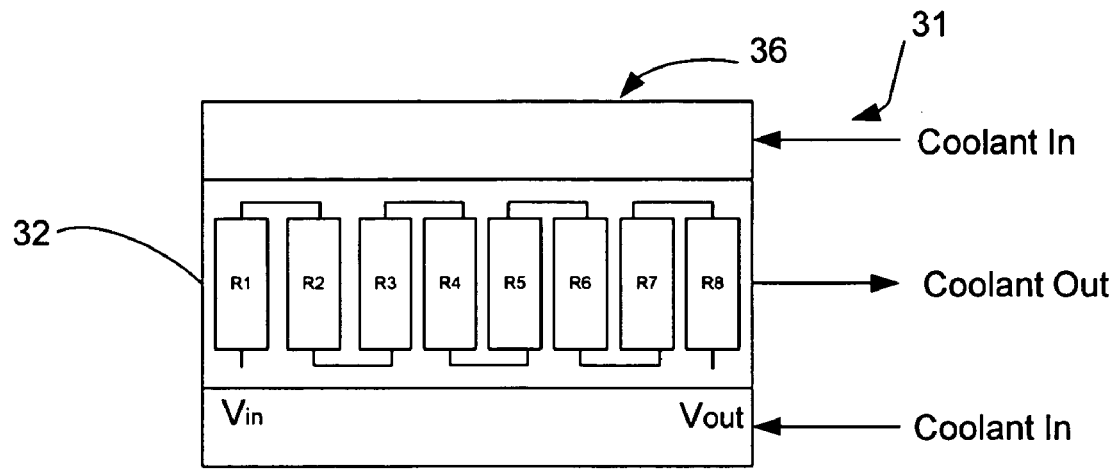
Figure 4I:
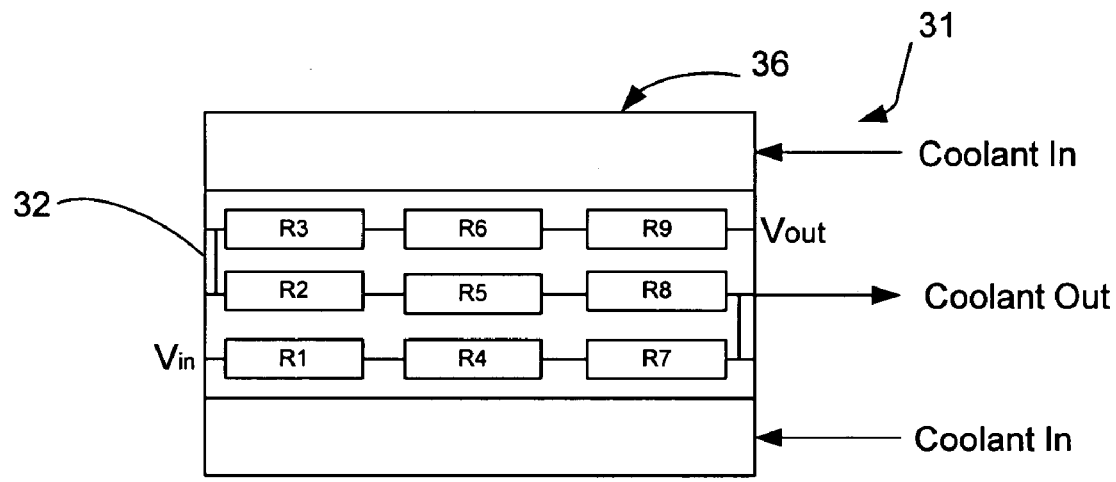
Figure 5:
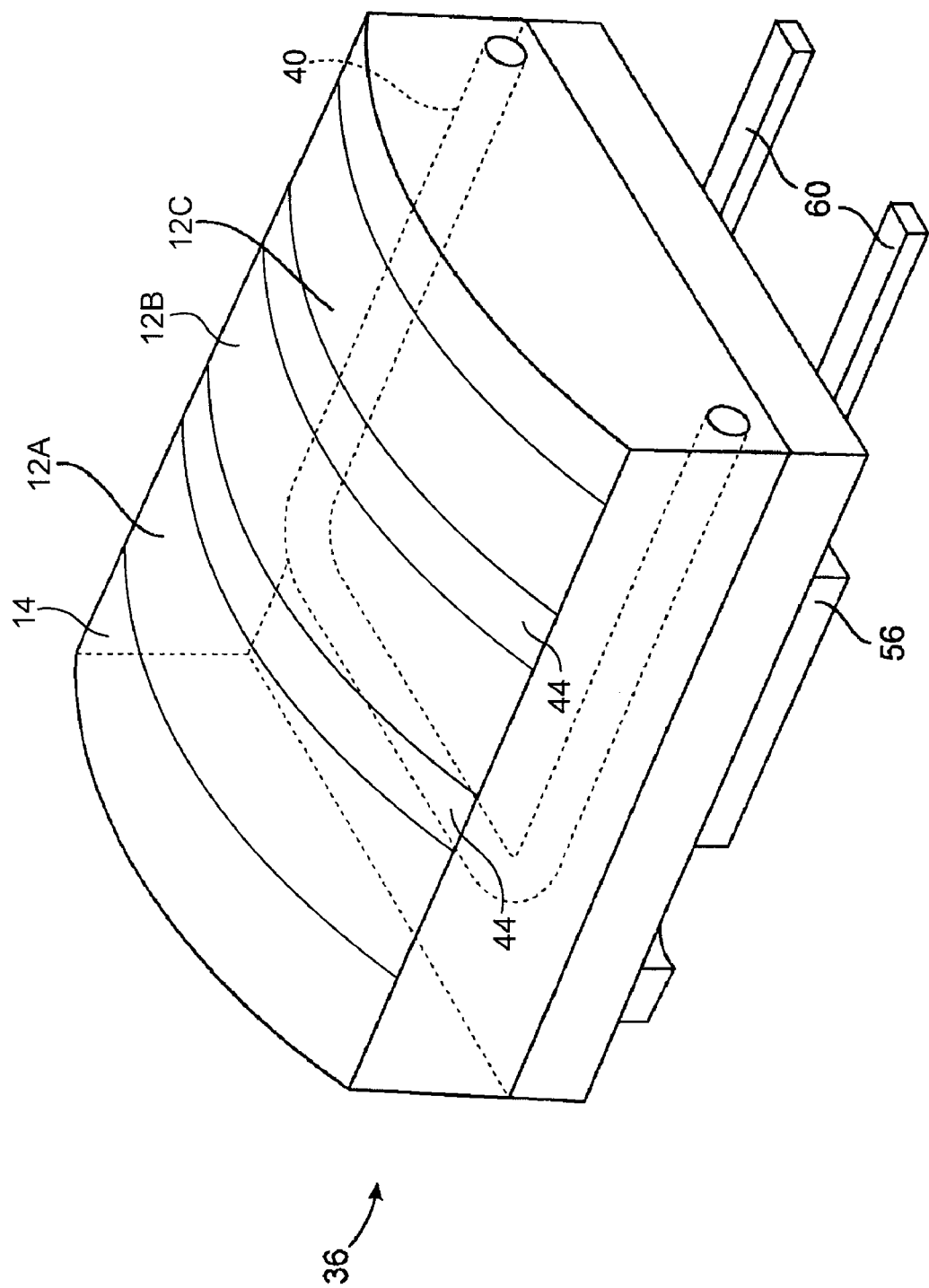
FIG. 5 illustrates a looped path of a coolant through a distal portion of the applicator of FIG. 2.

Referring now to FIGS. 5, 4B and 4C, the flow rate of the coolant will vary depending on the temperature of the coolant, the type of coolant used, the desired temperature at the contact surface, the type of procedure being performed, or the like. The coolant flow should also be selected to be great enough to accommodate all of the anticipated heat loads during the heat treatment. For example, when treating incontinence with a maximum therapeutic RF energy level of 50 W and the coolant is a R134a gas, the flow rate of the coolant is typically between about 5 and about 25 grams per second, and preferably between about 15 and about 20 grams per second. Such flow rates are chosen such that at the chosen flow rate the coolant is able to compensate for the maximum RF heating power levels. As can be appreciated, for other coolants and for other energy levels, the flow rate may be higher or lower.

FIGS. 5, 4B, and 4C illustrate two configurations of a coolant flow that are encompassed by the present invention. As can be appreciated, such configurations are merely examples and should not be construed to limit the scope of the present invention. While only one heating element 56 is illustrated in FIG. 5, it should be appreciated that any number of heating elements 56 may be used and the heating elements 56 may be placed in a variety of different patterns so as to provide substantially even cooling over the contact surface 14.

In the illustrated embodiment in FIG. 5, the path enters the distal portion and loops back around from the end and exits the distal portion as the outflow port 48. While such a loop configuration provides adequate cooling, the cooling is slightly asymmetrical across the electrode surface—about a 5° C. differential across the contact surface between the point where the coolant enters the distal portion and the point where the coolant exits the distal portion.

As shown in FIGS. 4B and 4C the flow path preferably takes on a path that provides more symmetrical cooling across the contact surface. In one embodiment, conduit 40 takes on the form of a serpentine path in which coolant is delivered through the distal portion 36 so as to substantially evenly control the temperature differential over the contact surface. For example, in the illustrated embodiment, the coolant is delivered into a left and right conduit simultaneously and the coolant is flowed in a zig-zag or serpentine pattern toward the middle of the applicator body where coolant exits the distal portion of the applicator body. Applicants have found that a serpentine conduit configuration in combination with appropriately positioned heating element(s) provide an improved method of evenly cooling the contact surface.

The coolant maintains a cooled tissue region on and around each electrode surface 14 below a maximum safe tissue temperature, typically being below about 45° C., and preferably between approximately 0° C. and about 40° C. To achieve the desired temperature in the intermediate tissue, the contact surface is typically cooled to a temperature between about −5° C. and about 3° C., and preferably about −2° C.

Figure 6:
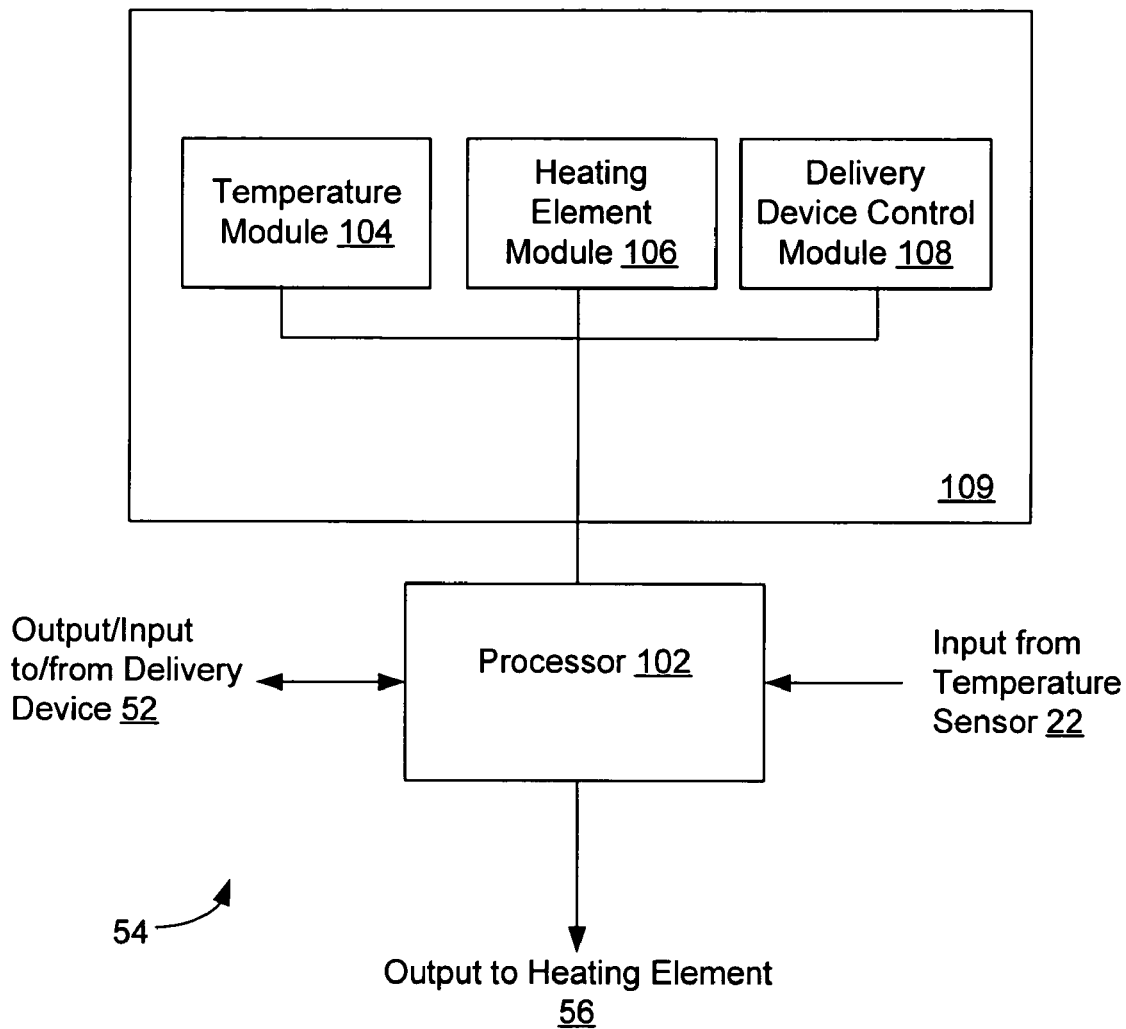
FIG. 6 schematically illustrates a control of the cooling assembly of FIG. 3.

FIG. 6 illustrates one embodiment of control 54 that controls the cooling algorithm of the present invention. Control 54 will typically include a processor 102 that is adapted to run a computer cooling algorithm stored in software modules 104, 106, 108 that are in a memory or other computer readable medium 109 that is accessible by the processor 102 of control 54. The computer readable medium may take the form of a hard drive, optical drive, such as a CD-ROM, or the any other conventional computer-readable medium. As can be appreciated, the illustrated code modules are merely illustrative, and the present invention may comprise a variety of other code modules for performing other aspects of the present invention. Moreover, it should be appreciated however, that instead of software modules, control 54 may include hardware modules or a combination of software and hardware to carry out the methods of the present invention.

Processor 102 will be in communication with temperature sensors 22, and may send control signals to direct the flow of the coolant in delivery device 52 and the power delivered to heating element 56. Such parameters are typically based at least in part on a temperature signal sensed by temperature sensors 22. In some embodiments, delivery of the coolant may be manually controlled by the user, if desired. In such embodiments, controller will not have a module for controlling the delivery of the coolant.

The temperature sensing may be provided using temperature sensors positioned on the distal end 36 of the catheter body (not shown) and/or needle 24 that carries one or more temperature sensors 22 (FIG. 2). Temperature sensor 22 may sense the temperature of the electrodes, the target tissue, the tissue at the tissue/electrode interface, and/or the intermediate tissue.

In exemplary embodiments, a temperature of the target tissue and/or the intermediate tissue may be monitored before the delivery of energy and during the delivery of energy using one or more temperature sensors on the applicator body and/or a needle assembly carrying one or more temperature sensors. It should be appreciated however, that in other embodiments, instead of temperature sensors, the needle can carry other sensors to monitor other characteristics of the tissue, and the temperature of the coolant may be based on such measured characteristics.

Temperature is measured via a thermocouple or RTD sensor that is positioned on or along an electrode surface. A higher than desired temperature is adjusted by limiting power supplied to the resistive heating element so as to allow the constantly flowing coolant to lower the temperature to the desired level. An under temperature condition is controlled by raising the power supplied to the resistive heating element so as to heat the distal end of the applicator and/or constantly flowing coolant to a higher temperature, and thus raise the temperature of the tissue contacting surface 14 and/or intermediate tissue. The amount of power, (wattage) supplied to the resistive heater may be adjusted either by varying voltage, current, or total power-on via pulsed relay to control % power supplied.

Figure 7:
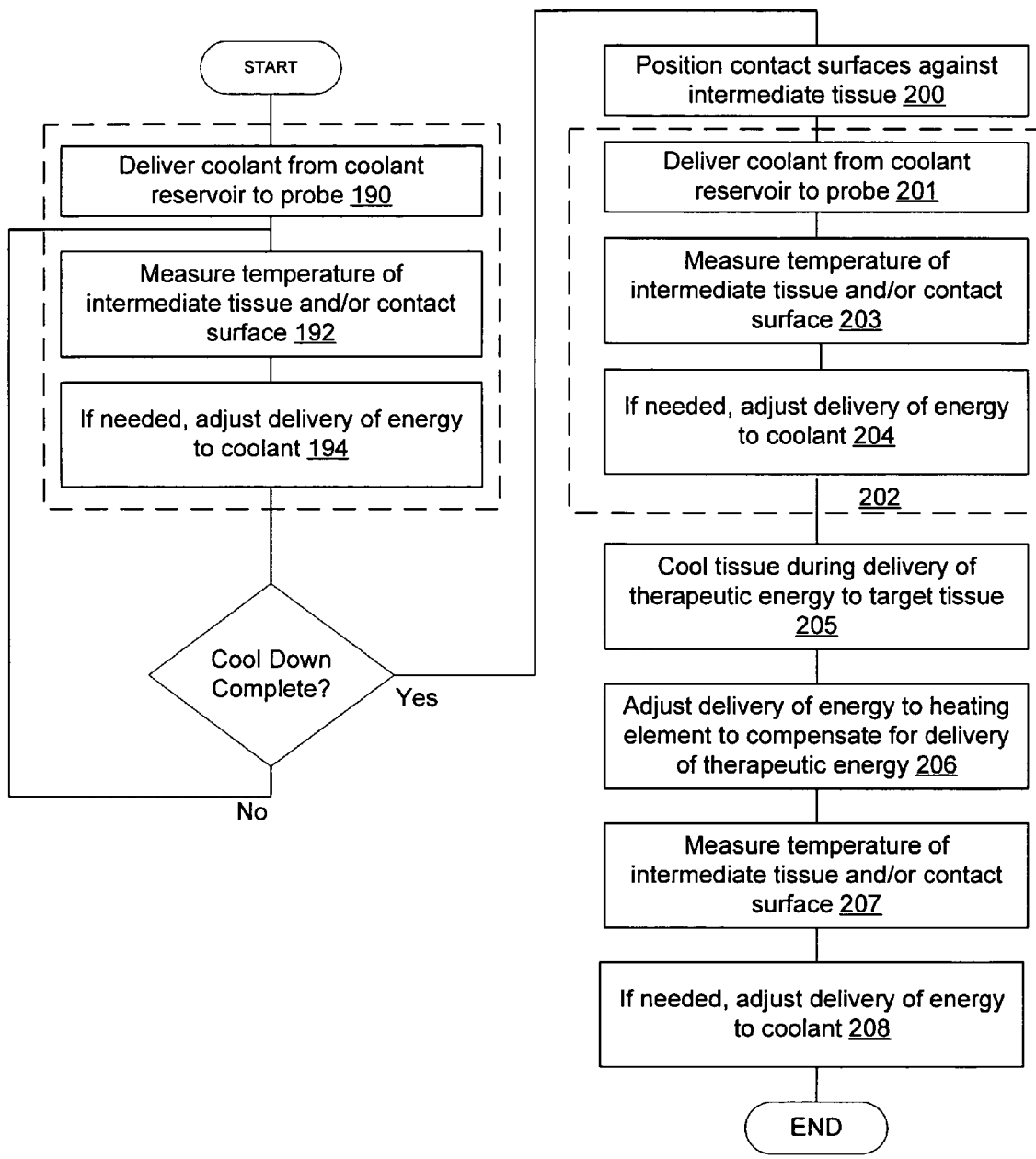
FIG. 7 schematically illustrates a method incorporated by the present invention.

FIG. 7 illustrates one method that may be carried out by the control 54 of FIG. 6 or other controls configured to carry out the methods of the present invention. At 200, a delivery device moves the coolant from a coolant reservoir and through the fluid conduit in the applicator. The flow rate of the coolant may be monitored by processor 102 and displayed on a display on a console or on the applicator. The parameters of the coolant temperature and coolant flow rate may be automatically controlled by delivery device control module 108 being run by processor 102. Alternatively, the coolant temperature and flow rate may be manually controlled by a user with a mechanical device, such as a valve.

Prior to use on the patient, the coolant flow is started by switch or other input device from the physician (step 190). The system measures the temperature of the contact surface using a temperature sensor just below the contact surface (step 192). During initial cooling of the applicator, the temperature is at or near room temperature and the control is delivering no power to the counter heating resistor(s). As the temperature approaches the set point value, the counter heating resistor(s) start to receive power to bring the final temperature smoothly to the set point value. If the set point value range is not met, the energy delivered to the heating resistor is adjusted (step 194). Once the set point value is within a small arbitrary range around the set point value and has remained in this range for a short time interval, the physician may perform a test of the needle thermocouple. One method of testing the thermocouple is by extending the needle. The controller then looks for a temperature rise in the thermocouple within the needle as the needle moves into the room temperature air. If this test passes, a further test is made by applying low level RF power to the applicator electrodes while the applicator is still in air to make sure that the electrodes are properly connected. If the cool down tests are not complete, steps 192 and 194 are repeated. Once these cool down tests are complete (the cooling control system remains operational throughout these tests) the physician then places the contact surfaces of the applicator 30 against the intermediate tissue (step 200). In one embodiment, the distal portion of the applicator is inserted transvaginally and placed against the intermediate tissue in the vagina. The coolant flow may optionally be used to pre-cool the intermediate tissue according to a predetermined pre-cooling regimen (step 202). In such embodiments, the coolant is delivered from the coolant reservoir and to the applicator through conduit 40 (step 201). The temperature of the intermediate tissue and/or the contact surfaces may be measured to determine if the temperatures are within a desired range (step 203). If adjustments to the temperature are needed, energy may be delivered to one or more heating elements 56 to bring the measured temperatures to the desired range (step 204). As can be appreciated however, in other embodiments, no pre-cooling may be performed, and the coolant may be flowed through the conduit 40 only during the delivery of the therapeutic heating energy (steps 205, described below).

Control 18 may run a variety of pre-treatment tests on the applicator 30 to ensure that the proper conditions for the procedure are present. For example, as described in co-pending, commonly owned U.S. patent application Ser. No. 10/768,780, entitled "Heating Method for Tissue Contraction", filed concurrently herewith (the complete disclosure of which is incorporated herein by reference), the control may test the tissue impedance to ensure that the electrodes are properly contacting the intermediate tissue.

When the user is ready to deliver the therapeutic energy to the target tissue, the coolant flow may be started (or maintained—if pre-cooling is performed) (step 205). Optionally during the therapeutic heating of the target tissue, the energy delivered to the heating element may be automatically reduced by control 54, since the energy delivered to electrodes tends to increase a temperature of the contact surface (e.g., electrodes 12) (step 206).

Concurrently therewith, the temperature of the intermediate tissue, target tissue, and/or contact surfaces of the applicator may be measured by one or more temperature sensors (step 207). The temperature signal may be processed at the processor 102 by temperature module 104. At 208, the processor determines if the intermediate tissue and/or contact surface of the applicator are within a desired temperature range. If the measured temperature is within the desired temperature range, the processor will typically not change any aspects of the cooling regimen. If however, the measured temperature(s) are not within the desired temperature range, processor 102 may send a signal to heating element 56 and/or delivery device 52 to change aspects of the cooling program to bring the temperature to within the desired range. For example, the processor may send a signal to adjust a flow rate of the coolant, a signal to globally change a temperature of the coolant, or a signal to locally change of the temperature of the coolant by adjusting the delivery of energy to a heating element. The monitoring of the temperature and the local adjustment of the temperature of the coolant may be repeated until the therapeutic heating is complete.

Figure 8:
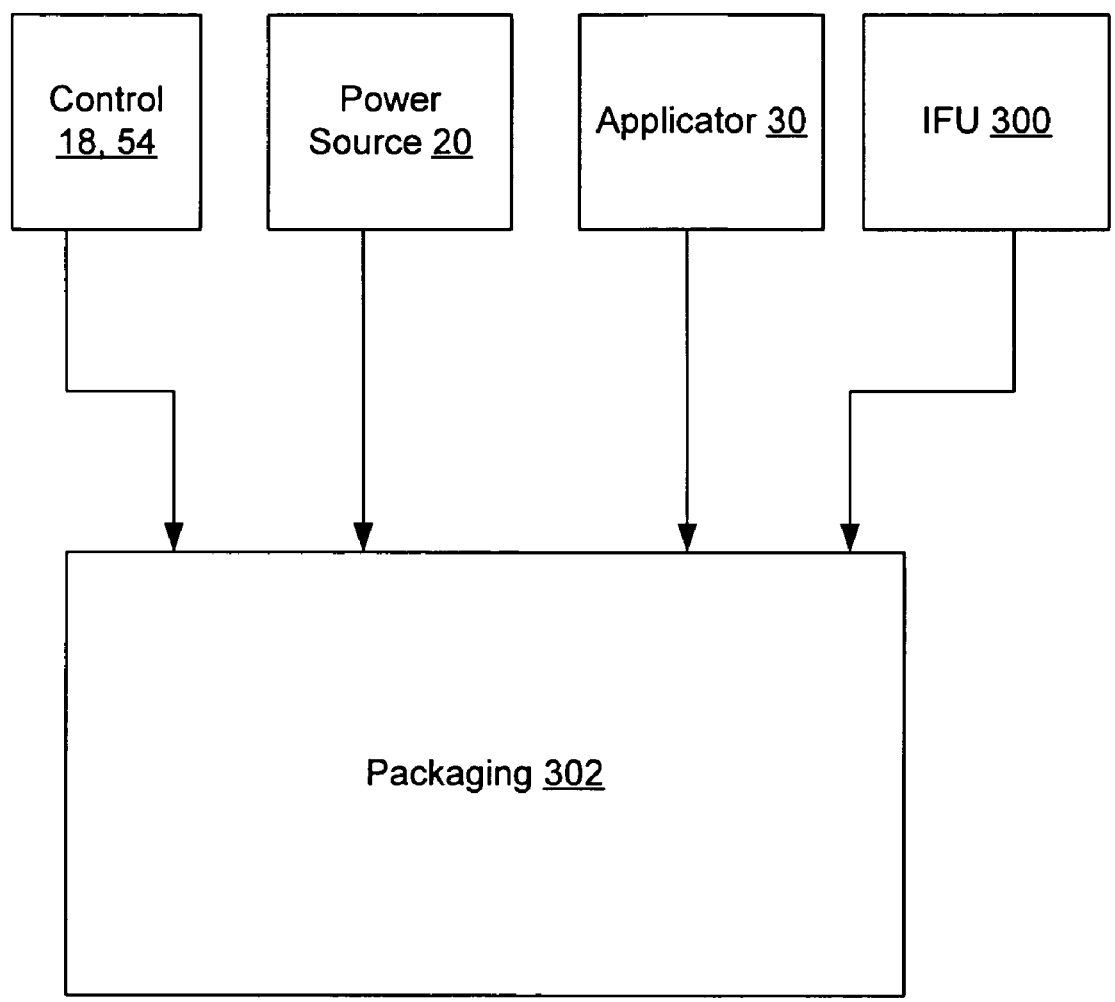
FIG. 8 schematically illustrates a kit of the present invention.

FIG. 8 illustrates a kit according to an embodiment of the present invention. The kit may include an applicator 30 and instructions for use 300, and one or more packages 302. Applicator 30 will generally be as described above, and the instruction for use (IFU) 300 will set forth any of the methods described above. Package 302 may be any conventional medical device packaging, including pouches, trays, boxes, tubes, or the like. The instructions for use 300 will usually be printed on a separate piece of paper, but may also be printed in whole or in part on a portion of the package 302. Optionally, the kit may include one or more controllers 18, 54 and/or a power source 30.

While particular forms of the invention have been illustrated and described, it will be apparent that various modifications can be made without departing from the spirit and scope of the invention. For example in other embodiments, instead of locally heating the coolant in the distal portion of the applicator, the coolant may be heated prior to entering the applicator or heating the coolant to a desired temperature while still in the coolant reservoir.

What is claimed is:

1. A method of controlling a temperature of an applicator body for treating incontinence, the method comprising:
providing an applicator body that comprises at least one electrode surface; delivering a coolant through a conduit in at least a portion of the applicator body at a substantially constant rate;
delivering sufficient heat energy, from within the applicator body, to the at least one electrode surface by energizing one or more heating elements so that the at least one electrode surface of the applicator body is cooled by the coolant to a desired temperature;
delivering therapeutic electrical energy through the at least one cooled electrode surface; and
contacting the at least one electrode surface against a surface adjacent pelvic support tissue.

2. The method of claim 1 wherein the cooled at least one electrode surface cools the contacted tissue that is adjacent the pelvic support tissue to a temperature between 0° C. and 40° C.

3. A method of controlling a temperature of an applicator body for treating incontinence, the method comprising:
providing an applicator body that comprises at least one electrode surface; delivering a coolant through a conduit in at least a portion of the applicator body at a substantially constant rate;
delivering sufficient heat energy, from within the applicator body, to the at least one electrode surface by energizing one or more heating elements so that the at least one electrode surface of the applicator body is cooled by the coolant to a desired temperature; and
delivering therapeutic electrical energy through the at least one cooled electrode surface, wherein the desired temperature is between about −5° C. and about 3° C.

4. The method of claim 3 wherein the desired temperature is about −2° C.

5. A method of controlling a temperature of an applicator body for treating incontinence, the method comprising:
providing an applicator body that comprises at least one electrode surface; delivering a coolant through a conduit in at least a portion of the applicator body at a substantially constant rate;
delivering sufficient heat energy, from within the applicator body, to the at least one electrode surface by energizing one or more heating elements so that the at least one electrode surface of the applicator body is cooled by the coolant to a desired temperature;
delivering therapeutic electrical energy through the at least one cooled electrode surface, wherein the coolant comprises a R134a refrigerant gas; and
contacting the at least one electrode surface against a surface adjacent pelvic support tissue.

6. The method of claim 1, 3 or 5 further comprising reducing a power level of the energy delivered to the heating element when the therapeutic heating energy is delivered to the at least one electrode surface.

7. A method of controlling a temperature of an applicator body for treating incontinence, the method comprising:
providing an applicator body that comprises at least one electrode surface; delivering a coolant through a conduit in at least a portion of the applicator body at a substantially constant rate;
delivering sufficient heat energy, from within the applicator body, to the at least one electrode surface by energizing one or more heating elements so that the at least one electrode surface of the applicator body is cooled by the coolant to a desired temperature;
delivering therapeutic electrical energy through the at least one cooled electrode surface;
monitoring a temperature of the at least one electrode surface;
adjusting a power level of the energy delivered to the heating element to maintain the at least one electrode surface of the applicator body at substantially the desired temperature; and
contacting the at least one electrode surface against a surface adjacent pelvic support tissue.

8. The method of claim 1, 3 or 5 wherein the heating element comprises a plurality of resistive heating elements positioned within the applicator body.

9. The method of claim 8 wherein the resistive heating element(s) contact a portion of the applicator body surrounding the coolant.

10. The method of claim 8 wherein the resistive heating element(s) are positioned in such as way as to minimize a flow related spatial distribution of temperature across the contact surface.

11. The method of claim 10 wherein the spatial distribution of temperature across the contact surface is reduced to less than about 2 degrees Celsius.

12. The method of claim 10 wherein the resistive heating element(s) are chosen to be at different wattage values in such a way as to reduce a flow related spatial distribution of temperature across the electrode surface while still permitting use of a single power source.

13. A method of controlling a temperature of an applicator body, the method comprising:
providing an applicator body that comprises at least one electrode surface; delivering a coolant through a conduit in at least a portion of the applicator body at a substantially constant rate;
delivering sufficient heat energy, from within the applicator body, to the at least one electrode surface by energizing one or more heating elements so that the at least one electrode surface of the applicator body is cooled by the coolant to a desired temperature; and
delivering therapeutic electrical energy through the at least one cooled electrode surface, wherein providing the applicator body comprises providing the coolant in a serpentine path for distributing the coolant substantially evenly over the contact surface.

14. An applicator that delivers energy comprising:
an applicator body comprising a proximal portion and a distal portion;
an electrode surface on the distal portion of the applicator body for delivering therapeutic electrical energy therethrough;
a conduit having a coolant that is delivered on a path through at least a part of the distal portion of the applicator body; and
one or more resistive heating elements thermally coupled, from within the applicator body, to the distal portion of the applicator body and entirely beneath the electrode surface to deliver a heating energy to the coolant in the conduit, wherein the energy is sufficient to heat the coolant so that the electrode surface is at a desired temperature, wherein the resistive heating elements are positioned to reduce a temperature differential across the electrode surface to less than about 2 degrees Celsius.

15. The applicator of claim 14 further comprising an RF power source coupled to the electrodes.

16. The applicator of claim 14 further comprising a control assembly that controls the delivery of the coolant and the heating element(s).

17. The applicator of claim 14 wherein the heating energy delivered to the heating element(s) is discontinued when the therapeutic energy is delivered to the electrodes.

18. The applicator of claim 14 further comprising a power supply coupled to the heating element(s), wherein the power supply is controlled with a temperature control algorithm.

19. The applicator of claim 14 wherein the electrode surface defines a proximal end and a distal end, wherein the heating elements are positioned to deliver more energy toward the proximal end of the electrode surface.

20. The applicator of claim 14 wherein a flow of the coolant is substantially constant.

21. The applicator of claim 14 wherein the desired temperature of the electrode-surface is between about −5° C. and about 3° C.

22. The applicator of claim 14 wherein the coolant comprises a R134a refrigerant gas.

23. The applicator of claim 14 further comprising a temperature sensor that monitors a temperature of the electrode surface.

24. An applicator that delivers energy comprising:
an applicator body comprising a proximal portion and a distal portion;
an electrode surface on the distal portion of the applicator body for delivering therapeutic electrical energy therethrough;
a conduit having a coolant that is delivered on a path through at least a part of the distal portion of the applicator body, wherein the coolant path through the distal portion of the applicator is a serpentine path; and
one or more heating elements thermally coupled, from within the applicator body, to the distal portion of the applicator body to deliver a heating energy to the coolant in the conduit, wherein the energy is sufficient to heat the coolant so that the electrode surface is at a desired temperature, and wherein the coolant comprises a R134a refrigerant gas.

25. A system for heating a pelvic support tissue adjacent an intermediate tissue, the system comprising:
a body comprising one or more electrodes oriented for contacting the intermediate tissue adjacent the pelvic support tissue;
a control system coupled to a power source and to the electrode(s), the control system adapted to selectively energize the electrode(s) so as to deliver a therapeutic heating energy through the intermediate tissue to the pelvic support tissue; and
a cooling assembly configured to control a temperature of the electrode(s), wherein the cooling assembly comprises:
a flow conduit positioned in the body to deliver a coolant adjacent the electrode(s);
a heating element positioned entirely under the electrode(s) and flow conduit to deliver energy to the flow conduit from within the body;
a temperature sensor positioned adjacent the electrode that measures a temperature of the electrode, wherein the coolant comprises a R134a gas.

26. The system of claim 25 further comprising the power source, wherein the power source is an RF power source.

27. The system of claim 25 wherein the temperature sensor comprises a thermocouple.

28. A method of controlling a temperature of an applicator body, the method comprising:
providing an applicator body that comprises at least one electrode surface; delivering a coolant through a conduit in at least a portion of the applicator body at a substantially constant rate;
delivering sufficient heat energy, from within the applicator body, to the at least one electrode surface by energizing one or more heating elements so that the at least one electrode surface of the applicator body is cooled by the coolant to a desired temperature, wherein the heating element comprises a plurality of resistive heating elements positioned within the applicator body, and wherein the resistive heating element(s) contact a portion of the applicator body surrounding the coolant; and
delivering therapeutic electrical energy through the at least one cooled electrode surface, wherein the coolant comprises a R134a refrigerant gas.

29. A method of controlling a temperature of an applicator body, the method comprising:

providing an applicator body that comprises at least one electrode surface; delivering a coolant through a conduit in at least a portion of the applicator body at a substantially constant rate;

delivering sufficient heat energy, from within the applicator body, to the at least one electrode surface by energizing one or more heating elements so that the at least one electrode surface of the applicator body is cooled by the coolant to a desired temperature, wherein the heating element comprises a plurality of resistive heating elements positioned within the applicator body in such a way as to minimize a flow related spatial distribution of temperature across the contact surface; and delivering therapeutic electrical energy through the at least one cooled electrode surface, wherein the coolant comprises a R134a refrigerant gas.

30. A method of controlling a temperature of an applicator body, the method comprising:

providing an applicator body that comprises at least one electrode surface; delivering a coolant through a conduit in at least a portion of the applicator body at a substantially constant rate;

delivering sufficient heat energy, from within the applicator body, to the at least one electrode surface by energizing one or more heating elements so that the at least one electrode surface of the applicator body is cooled by the coolant to a desired temperature, wherein the heating element comprises a plurality of resistive heating elements positioned within the applicator body in such a way as to minimize a flow related spatial distribution of temperature across the contact surface, the spatial distribution of temperature being reduced to less than about 2 degrees Celsius; and delivering therapeutic electrical energy through the at least one cooled electrode surface, wherein the coolant comprises a R134a refrigerant gas.

31. An applicator that delivers energy comprising:

an applicator body comprising a proximal portion and a distal portion;

an electrode surface on the distal portion of the applicator body for delivering therapeutic electrical energy therethrough;

a conduit that delivers a coolant on a path through at least a part of the distal portion of the applicator body, wherein the coolant path through the distal portion of the applicator is a serpentine path; and one or more heating elements thermally coupled, from within the applicator body, to the distal portion of the applicator body and entirely beneath the electrode surface to deliver a heating energy to the coolant in the conduit, wherein the energy is sufficient to heat the coolant so that the electrode surface is at a desired temperature.

* * * * *